United States Patent
Konieczynski et al.

(10) Patent No.: US 7,651,517 B2
(45) Date of Patent: *Jan. 26, 2010

(54) BONE PLATE AND RESILIENT SCREW SYSTEM ALLOWING BI-DIRECTIONAL ASSEMBLY

(75) Inventors: David D. Konieczynski, Needham, MA (US); Thomas V. Doherty, Latham, NY (US)

(73) Assignee: Depuy Acromed, Inc., Raynham, MA (US)

( * ) Notice: Subject to any disclaimer, the term of this patent is extended or adjusted under 35 U.S.C. 154(b) by 103 days.

This patent is subject to a terminal disclaimer.

(21) Appl. No.: 11/279,613

(22) Filed: Apr. 13, 2006

(65) Prior Publication Data

US 2006/0241616 A1     Oct. 26, 2006

Related U.S. Application Data

(63) Continuation of application No. 10/335,539, filed on Dec. 31, 2002, now Pat. No. 7,048,739.

(51) Int. Cl.
*A61B 17/04* (2006.01)
*A61B 17/86* (2006.01)

(52) U.S. Cl. .................. 606/305; 606/308; 606/287; 606/288

(58) Field of Classification Search .......... 606/69–73, 606/295, 286, 291, 293, 300, 305, 319, 320, 606/308, 281, 287, 288
See application file for complete search history.

(56) References Cited

U.S. PATENT DOCUMENTS

| | | | |
|---|---|---|---|
| 3,604,414 A | 9/1971 | Borges | |
| 4,388,921 A | 6/1983 | Sutter et al. | |
| 4,484,570 A | 11/1984 | Sutter | |
| 4,509,890 A | 4/1985 | Hill | |
| 4,621,961 A | 11/1986 | Gulistan | |
| 5,108,395 A | 4/1992 | Laurain | |
| 5,147,361 A | 9/1992 | Ojima | |
| 5,180,381 A | 1/1993 | Aust | |
| 5,246,443 A | 9/1993 | Mai | |
| 5,324,290 A | 6/1994 | Zdeblick | |

(Continued)

FOREIGN PATENT DOCUMENTS

WO    WO-02/09605    2/2002

(Continued)

OTHER PUBLICATIONS

Product Brochure "Introducing EBI Vuelock, Anterior Cervical Plate System" EBI, a Biomet Company, 2001.

(Continued)

*Primary Examiner*—Pedro Philogene

(57) ABSTRACT

Bone screws and bone plates are provided that offer the surgeon the ability to either assemble the screws to the plate, or the plate to the screws, depending on the surgeon's preference and the patient's circumstances. The bone screws and bone plates of the present invention include a combination of geometric configurations that allow the screws and plates to fit together from different assembly directions. Additionally, the bone screws and bone plates can include material resilience features to allow expansion/contraction during assembly to allow bi-directional attachment to one another.

19 Claims, 17 Drawing Sheets

U.S. PATENT DOCUMENTS

| | | | |
|---|---|---|---|
| 5,334,203 A | 8/1994 | Wagner | |
| 5,364,399 A | 11/1994 | Lowery | |
| 5,395,372 A | 3/1995 | Holt | |
| 5,423,826 A | 6/1995 | Coates et al. | |
| 5,549,612 A | 8/1996 | Yapp | |
| 5,578,034 A | 11/1996 | Estes | |
| 5,601,553 A | 2/1997 | Trebing | |
| 5,603,713 A | 2/1997 | Aust | |
| 5,607,428 A | 3/1997 | Lin | |
| 5,616,142 A | 4/1997 | Yuan et al. | |
| 5,616,144 A | 4/1997 | Yapp | |
| 5,630,817 A * | 5/1997 | Rokegem et al. | 606/269 |
| 5,634,926 A | 6/1997 | Jobe | |
| 5,676,666 A | 10/1997 | Oxland | |
| 5,681,311 A | 10/1997 | Foley | |
| 5,683,393 A | 11/1997 | Ralph | |
| 5,735,853 A | 4/1998 | Olerud | |
| 5,851,207 A | 12/1998 | Cesarone | |
| 5,865,847 A | 2/1999 | Kohrs et al. | |
| 5,902,303 A | 5/1999 | EckhOF | |
| 5,904,683 A | 5/1999 | Pohndorf et al. | |
| 5,931,838 A | 8/1999 | Vito | |
| 5,951,558 A | 9/1999 | Fiz | |
| 5,954,722 A | 9/1999 | Bono | |
| 6,017,345 A | 1/2000 | Richelsoph | |
| 6,030,389 A | 2/2000 | Wagner | |
| 6,036,693 A * | 3/2000 | Yuan et al. | 606/61 |
| 6,059,785 A | 5/2000 | Schavan et al. | |
| 6,139,316 A | 10/2000 | Sachdeva | |
| 6,139,550 A | 10/2000 | Michelson | |
| 6,152,927 A | 11/2000 | Farris | |
| 6,193,721 B1 | 2/2001 | Michelson | |
| 6,206,882 B1 | 3/2001 | Cohen | |
| 6,224,602 B1 | 5/2001 | Hayes | |
| 6,235,028 B1 | 5/2001 | Brumfield | |
| 6,235,034 B1 | 5/2001 | Bray | |
| 6,241,731 B1 | 6/2001 | Fiz | |
| 6,258,089 B1 | 7/2001 | Campbell | |
| 6,261,291 B1 | 7/2001 | Talaber et al. | |
| 6,273,889 B1 | 8/2001 | Richelsoph | |
| 6,283,969 B1 * | 9/2001 | Grusin et al. | 606/280 |
| 6,293,949 B1 | 9/2001 | Justis | |
| 6,303,136 B1 | 10/2001 | Li | |
| 6,303,139 B1 | 10/2001 | Passi | |
| 6,331,179 B1 | 12/2001 | Freid | |
| 6,336,928 B1 | 1/2002 | Guerin | |
| 6,342,055 B1 | 1/2002 | Eisermann | |
| 6,342,057 B1 | 1/2002 | Brace et al. | |
| 6,379,364 B1 | 4/2002 | Brace et al. | |
| 6,413,259 B1 | 7/2002 | Lyons | |
| 6,428,542 B1 | 8/2002 | Michelson | |
| 6,503,250 B2 | 1/2003 | Paul | |
| 6,527,776 B1 | 3/2003 | Michelson | |
| 6,533,786 B1 | 3/2003 | Needham | |
| 6,558,423 B1 | 5/2003 | Michelson | |
| 6,565,571 B1 | 5/2003 | Jackowski et al. | |
| 6,595,993 B2 | 7/2003 | Donno | |
| 6,626,907 B2 | 9/2003 | Campbell et al. | |
| 6,652,525 B1 | 11/2003 | Assaker | |
| 6,669,473 B1 | 12/2003 | Maino et al. | |
| 6,669,700 B1 | 12/2003 | Farris | |
| 6,695,846 B2 | 2/2004 | Richelsoph | |
| 6,755,833 B1 | 6/2004 | Paul | |
| 6,890,334 B2 * | 5/2005 | Brace et al. | 606/69 |
| 6,893,444 B2 * | 5/2005 | Orbay | 606/281 |
| 7,001,389 B1 * | 2/2006 | Navarro et al. | 606/71 |
| 7,048,739 B2 * | 5/2006 | Konieczynski et al. | 606/73 |
| 2001/0041894 A1 | 11/2001 | Campbell | |
| 2002/0082606 A1 | 6/2002 | Suddaby | |
| 2002/0147450 A1 | 10/2002 | Lehuec | |
| 2003/0040749 A1 | 2/2003 | Grabowski | |
| 2003/0060828 A1 | 3/2003 | Michelson | |
| 2003/0135213 A1 | 7/2003 | Luehuec | |
| 2003/0187440 A1 | 10/2003 | Richelsoph | |
| 2003/0187442 A1 | 10/2003 | Richelsoph | |
| 2003/0233098 A1 | 12/2003 | Markworth | |
| 2004/0015169 A1 | 1/2004 | Gause | |
| 2004/0015174 A1 | 1/2004 | Null | |
| 2004/0030340 A1 | 2/2004 | Pisharodi | |
| 2004/0034352 A1 | 2/2004 | Needham | |
| 2004/0034354 A1 | 2/2004 | Paul | |
| 2004/0087951 A1 | 5/2004 | Khalili | |
| 2004/0092947 A1 | 5/2004 | Foley | |
| 2004/0097935 A1 | 5/2004 | Richelsoph | |
| 2004/0133205 A1 | 7/2004 | Thramann | |
| 2005/0049593 A1 | 3/2005 | Duong | |

FOREIGN PATENT DOCUMENTS

| | | |
|---|---|---|
| WO | WO-02/45592 | 6/2002 |
| WO | WO-03/007826 | 1/2003 |
| WO | WO-03/024344 | 3/2003 |

OTHER PUBLICATIONS

Web Page www.ebiomedical.com/products/spine/vuelock.html, "EBI VueLock, Anterior Cervical Plate System" EBI, A Biomet Company, 2002.

Product Brochure "Introducing the Low Profile ZEPHIR Anterior Cervical Plate System" Medtronic, Sofannor Danek.

Web Page www.sofamordanek.com "Zephir Anterior Cervical Plate System" Medtronic Sofamor Danek.

Product Brochure "PEAK Polyakial Cervical Plating System" DuPuy Acromed, Inc., 1999.

Producet Brochure "PEAK Anterior Compression Plate" DePuy Acromed, Inc., 1996.

Product Brochure "The Titanium Buttress Locking Plate" Synthes Spine, 1997.

Product Brochure "AcroMed Special Products" DePuy Acromed, Inc., 1998.

Product Brochure "Surgical Technique PROFILE Anterior Thoraco-Lumbar Plating System" DePuy Acromed, Inc. 2002.

Product Brochure "ABC Anterior Cervical Plating System" AESCULAP, 1999. Li.

Product Brochure "Zephir Anterior Cervical Plate System Surgical Technique" Medtronic Sofamor Danek, 2002.

* cited by examiner

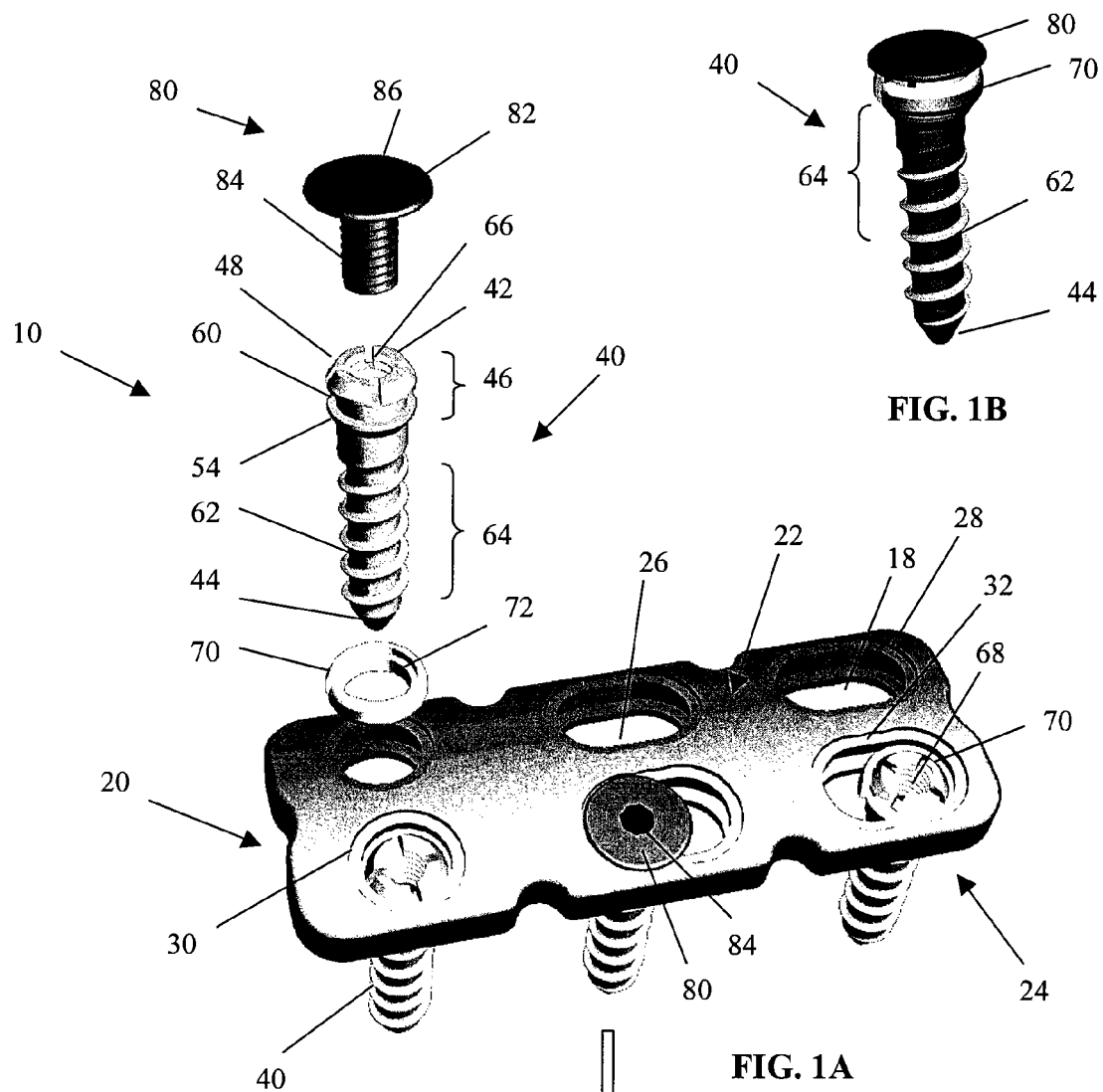
FIG. 1B
FIG. 1A
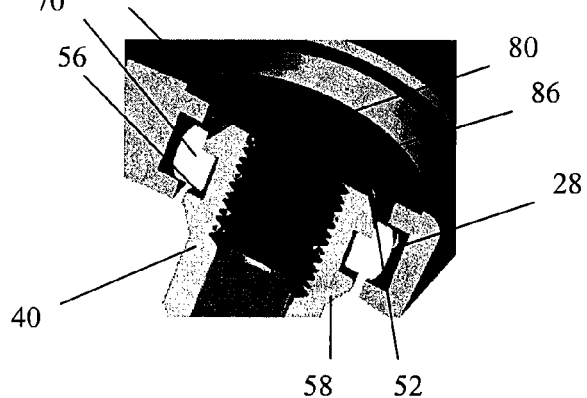
FIG. 1C

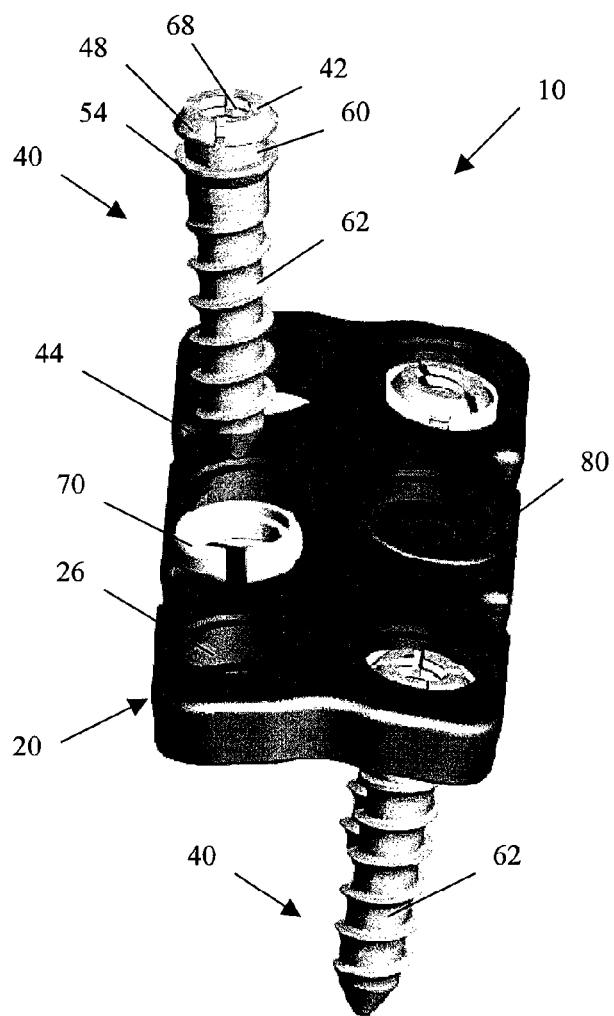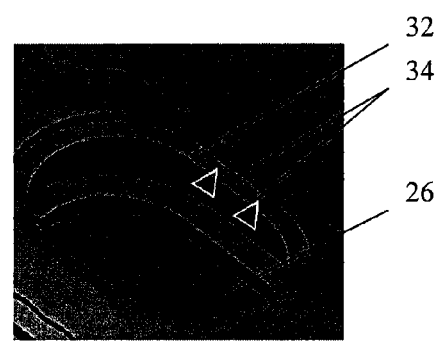
FIG. 2B
FIG. 2A

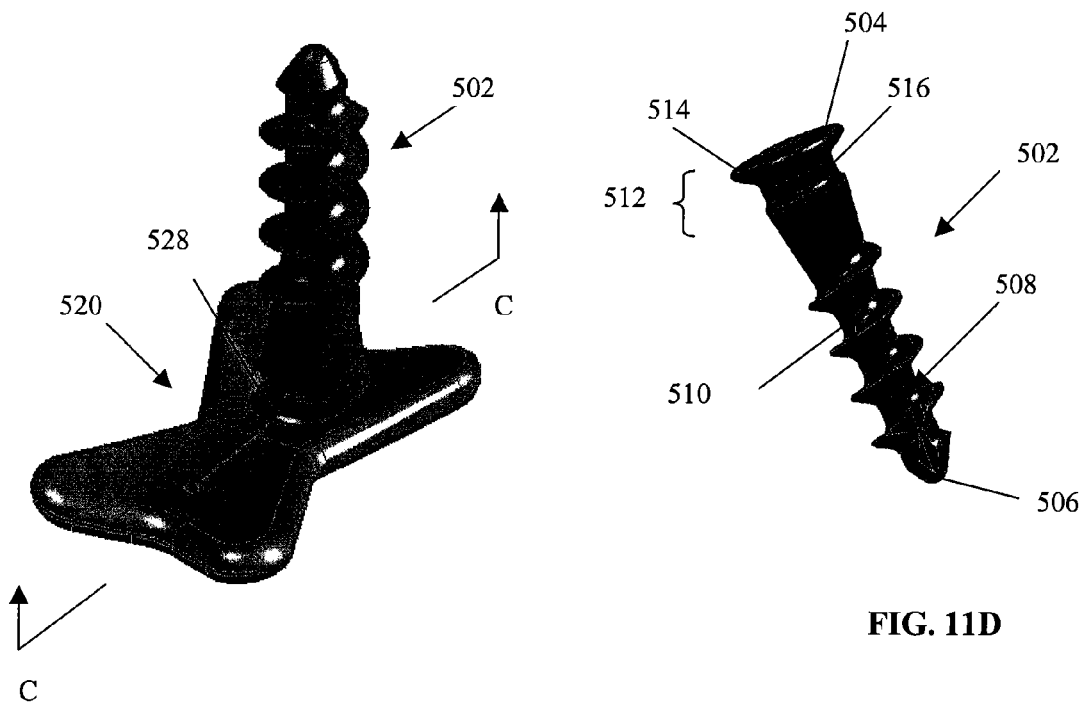
FIG. 11D
FIG. 11C
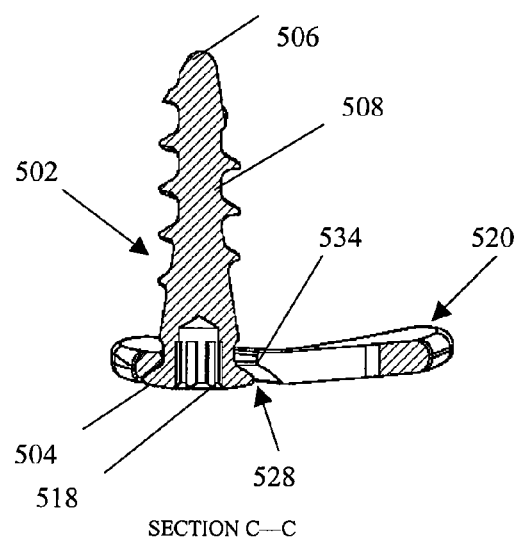
SECTION C—C
FIG. 11E

FIG. 12C  FIG. 12D

BONE PLATE AND RESILIENT SCREW SYSTEM ALLOWING BI-DIRECTIONAL ASSEMBLY

CROSS-REFERENCE TO RELATED APPLICATIONS

This application is a continuation of U.S. patent application Ser. No. 10/335,539 filed on Dec. 31, 2002 and entitled "Bone Plate and Screw System Allowing Bi-Directional Assembly," which is hereby incorporated by reference in its entirety.

FIELD OF THE INVENTION

The present invention relates to bone fixation devices used in orthopedic and spinal surgeries for stabilizing and immobilizing bone fragments. More particularly, this invention relates to a bone plate and screw system that allows both a plate first or anchors first approach to implanting the bone plate.

BACKGROUND OF THE INVENTION

Bone fixation devices are useful for promoting the proper healing of injured or damaged vertebral bone segments caused by trauma, tumor growth, or degenerative disc disease. These external fixation devices immobilize the injured bone segments to ensure the proper growth of new osseous tissue between the damaged segments. External bone fixation devices such as these often include internal bracing and instrumentation to stabilize the spinal column to facilitate the efficient healing of the damaged area without deformity or instability, while minimizing any immobilization and postoperative care of the patient.

One type of external bone fixation device is an osteosynthesis plate, more commonly referred to as a bone plate, that can be used to immobilize adjacent skeletal parts such as vertebral bones. Typically, the fixation plate is a rigid metal or polymeric plate positioned to span bones or bone segments that require immobilization with respect to one another. The plate is fastened to the respective bones, using anchors such as bone screws, so that the plate remains in contact with the bones and fixes them in a desired position. Anterior cervical plates, for instance, can be useful in providing the mechanical support necessary to keep vertebral bodies in proper position and bridge a weakened or diseased area such as when a disc, vertebral body or spinal fragment has been removed. These anterior cervical plates usually include a rigid bone plate having a plurality of screw openings. The openings are either holes or slots that allow for freedom of screw movement. The bone plate is placed against the damaged vertebral bodies and bone screws are used to secure the bone plate to the spine, usually with the bone screws being driven into the vertebral bodies.

Currently, bone screws and bone plates allow either a plate first construction or an anchors first construction. That is, some bone screws and bone plates are constructed such that the bone plate is placed onto the intended area to be fixed, and then the bone screws are inserted through the plate to secure the plate to the bone segments. In other bone plate and screw systems, the screws are inserted into the bone segments first, then the plate is secured to the screws. One benefit of being able to apply a bone screw and plate system using such an anchors first approach is that the plate is not positioned in a manner that will block the surgeon's view of the implantation site. The surgeon is therefore able to better position the plate and manipulate around the patient's anatomy during implantation.

It would be desirable to provide bone screws and bone plate systems that are both easy to use and capable of bi-directional assembly using either a plate first or anchors first construction. Such a system would allow the clinician the flexibility to use either a plate first or an anchors first approach with the same bone screw and bone plate during surgery. One benefit of being able to apply a bone screw and plate system using an anchors first approach is that the plate is not positioned over the surgical site before inserting the screws, and so the plate does not obstruct the surgeon's view when implanting the screws. While it is possible to achieve flexibility and the aforementioned benefits with a two-part bone screw comprising a threaded nut and bone screw or post, a single-component bone screw is more desirable because it does not require intraoperative assembly and therefore has enhanced ease of use.

SUMMARY OF THE INVENTION

The present invention achieves the aforementioned goals by providing systems of single-component bone screws and bone plates that offer the surgeon the ability to either assemble the screws to the plate, or the plate to the screws, depending on the surgeon's preference and the patient's anatomical conditions. With this invention, the surgeon is given intraoperative flexibility regarding the approach taken when applying the system, allowing the clinician to use either a plate first or anchors first approach with the same screws and plate. The bone screws and bone plates of the present invention include a combination of geometric configurations that allow the screws and plates to fit together from different assembly directions. Additionally, the bone screws and bone plates can include material resilience features to allow expansion/contraction during assembly to enable bi-directional attachment one another. The various geometric configurations of the present system allow the bone plate and screws to accommodate different patient anatomies as the natural bones settle after implantation. The geometric configurations also provide the bone plate and screw system with selective biomechanical properties such as toggling, translation, and/or rotation to facilitate bone growth and healing.

In one exemplary system of the present invention, the bone plate and screw system comprises a bone plate for stabilizing bone segments, a screw configured for insertion into bone, and a resilient locking member for securing the bone plate to the screw. The bone plate has a first surface and a second, bone-contacting surface that is opposed to the first surface, and an aperture extending through the first and second surfaces. The aperture has a predefined shape and size, and is configured to receive the bone screw.

The bone screw of the present embodiment has a head region at a proximal end and an elongated body extending from the head region to a distal end of the screw. In one aspect of the invention, the head region is defined by a top flange, a bottom flange, and a groove extending therebetween, while the elongated body includes a threaded portion configured for insertion into bone. Additionally, the aperture of the bone plate includes a seating groove for capturing the resilient locking member.

The resilient locking member secures the bone plate to the implanted screw, and is sized and shaped to mate with the groove of the screw. For example, the resilient locking member can be an expandable snap ring. The entire system can be assembled together using either a plate first or an anchors first approach, with the latter being desirable for the advantages previously mentioned. Preferably, the entire system can be assembled together using both a plate first and an anchors first approach to provide the benefits associated with bi-directional assembly.

In another aspect of the invention, the bone screw of the present system has a head region defined by an upper surface, a lower surface, and a sidewall extending therebetween and connecting the upper and lower surfaces. The head region is located at a proximal end, while an elongated body extends from the head region to a distal end of the screw. The elongated body includes a threaded portion for insertion into bone. To secure the bone plate to the screw, a resilient locking member is provided having a top surface, a bottom surface, and an outer wall extending therebetween and connecting the top and bottom surfaces together.

The resilient locking member also includes a channel extending about its inner circumference, the channel being sized and shaped to capture the head region of the screw. Also, the resilient locking member can have a top surface which extends along a downward slope from an outer edge to an inner edge of the top surface, and a bottom surface which extends along an upward slope from an outer edge to an inner edge of the bottom surface. The chamfered features help to facilitate assembly of the bone plate and screw system.

In another exemplary system of the present invention, the bone plate and screw system comprises a bone plate for stabilizing bone segments and a resilient screw configured for insertion into bone. The bone plate has a first surface and a second, bone-contacting surface that is opposed to the first surface, and an aperture extending through the first and second surfaces. The aperture has a predefined shape and size, and is configured to receive the resilient screw. The aperture can be countersunk on either the first or second surface of the bone plate, or both, to accommodate a direct engagement with the bone screw.

The resilient screw of the present embodiment has a head region at a proximal end and an elongated body extending from the head region to a distal end of the screw. The elongated body includes a threaded portion for insertion into bone. In one aspect of the invention, the head region is defined by a top flange, an bottom flange, and a groove extending therebetween. At least one of the top and bottom flanges of the screw is resilient, such that the bone plate and screw system can be assembled together using either a plate first or an anchors first approach, with the latter approach being desirable to provide the benefits associated with an anchors first construction to the system. More preferably, the system can be assembled bi-directionally using both a plate first and an anchors first construction.

The present system can optionally include an attachment member for securing the bone plate to the screw. The optional attachment member can be sized and shaped to mate with the groove of the resilient screw. Further, the attachment member can be configured to be captured within a seating groove provided within the aperture of the bone plate. Attachment member can have a top surface which extends along a downward slope from an outer edge to an inner edge of the top surface, and a bottom surface which extends along an upward slope from an outer edge to an inner edge of the bottom surface. These chamfered surfaces help to facilitate assembly of the bone plate and screw system.

In another aspect of the invention, the resilient bone screw of the present system has a head region having a compressible diameter, the head region being defined by an upper surface, a lower surface, and a sidewall extending therebetween and connecting the upper and lower surfaces. The head region is located at a proximal end, while an elongated body extends from the head region to a distal end of the screw. The elongated body includes a threaded portion for insertion into bone. To secure the bone plate to the resilient screw, an optional attachment member can be provided having a top surface, a bottom surface, and an outer wall extending therebetween and connecting the top and bottom surfaces together. The attachment member also includes a channel extending about its inner circumference, the channel being sized and shaped to capture the head region of the resilient screw.

In yet another exemplary system of the present invention, the bone plate and screw system comprises a resilient bone plate for stabilizing bone segments, and a screw configured for insertion into bone. The bone plate has a body including a first surface and a second, bone-contacting surface that is opposed to the first surface. At least one resilient aperture having a predefined shape and size extends through the first and second surfaces. The aperture is configured to cooperate with a relief slit extending therefrom to allow the aperture to expand and contract to receive the bone screw. The relief slit can extend into a relief hole, or another aperture. The resilient bone plate of the present embodiment can include a plurality of resilient apertures, relief slits and relief holes.

The bone screw of the present embodiment has a head region at a proximal end and an elongated body extending from the head region to a distal end of the screw. In one aspect of the invention, the head region is defined by a top flange, a bottom flange, and a groove extending therebetween, while the elongated body includes a threaded portion for insertion into bone. The bone plate and screw system can be assembled together using either a plate first or an anchors first approach, with the latter approach being desirable to provide the benefits accorded with an anchors first approach as previously mentioned. Preferably, the system can be assembled bi-directionally using both a plate first and an anchors first construction.

In other features of the present invention, each of the plurality of apertures can be shaped like a hole or an oblong slot. The apertures are sized and shaped to receive screws configured to be inserted into bone. The screws can be used to anchor the bone plate to bone segments. Each of the screws has a head region at a proximal end. In one instance, the head region is defined by a top flange, a bottom flange, and a groove located between the top and bottom flanges and extending about the circumference of the head region. In another instance, the head region is defined by an upper surface, a lower surface, and a sidewall extending therebetween and connecting the upper and lower surfaces. An elongated body which includes a threaded portion extends from the head region to a distal end of the screw. In yet another instance, the head region includes a flange and a groove extending about the circumference of the head region. The body of the screw extends from the groove down to the distal end.

The bone screws of the present invention can be provided with a chamfered proximal surface of the top flange and/or a chamfered distal surface of the bottom flange. At least one of the top and bottom flanges can also have a compressible diameter to allow bi-directional attachment to the bone plate. For instance, the top and bottom flanges can include at least one vertical relief slit extending therethrough. To allow for anchors first construction in this embodiment, at least the top flange is resilient. Further, each screw can have an open head region, with a threaded bore extending from an upper surface of the head region. A threaded cap can be provided that is configured to engage with the threaded bore of the head region. The threaded cap can be captured within a nested region of the countersunk rim of the apertures. When threaded onto the head region, the threaded cap provides a smooth profile to the bone plate and screw system while at the same time limiting movement of the screw with respect to the bone plate.

To secure the bone plate to the screws, a plurality of resilient locking members are provided with the bone plate and screw system of the present invention. The resilient locking members are sized and shaped to mate with the grooves of the screws, and enable locking engagement of the bone plate to the screws. Each of the resilient locking members is configured to be disposed in a seating groove within the apertures of the bone plate. The resilient locking members can comprise expandable snap rings, or C-rings.

In one exemplary embodiment of the present invention, the seating groove of the bone plate includes a ratcheted edge along a side thereof. A resilient locking member comprising an expandable snap ring having a notched edge is also provided. The ratcheted edge of the seated groove is configured to mate with the notched edge of the expandable snap ring. The expandable snap ring can further include a channel extending about its inner circumference for capturing the head region of the screw. Alternatively, the expandable snap ring can be configured to nest around the groove of the screw. Such features provide the clinician with even more flexibility with respect to the manner of implementation.

The present invention also provides a bone screw which can be assembled to a bone plate in a plate first or anchors first approach. The bone screw comprises a head region at a proximal end of the bone screw. The head region is defined by a top flange, a bottom flange, and a groove extending therebetween about a circumference of the head region. An elongated body extends from the head region to a distal end of the screw. The elongated body can include a threaded portion configured for threading into bone. The proximal surface of the top flange and the distal surface of the bottom flange can be chamfered to facilitate the insertion of a locking member over the head region and into the groove. Preferably, at least one of the top and bottom flanges has a compressible diameter. Further, at least one of the top and bottom flanges includes at least one vertical slot extending through the flange. The head region can also include a threaded bore extending from a proximal end thereof.

Also provided is a method for assembling the bone plate and screw systems described above using an anchors first approach, wherein at least one screw is inserted into a bone segment to be fixed. A tapered post can be attached to the screw to facilitate alignment and placement of the bone plate over the bone screw. If a resilient locking member is to be used with the system, the locking member should be captured within the seating groove of the bone plate prior to assembly. Next, the bone plate (with the optional resilient locking member) is disposed over the tapered post and aligned with the implanted screw. The bone plate is slid down the tapered post and onto the implanted screw. The taper of the post will facilitate the expansion of either the bone plate aperture or the resilient locking member, depending on which system is being used. After the aperture or locking member has been maneuvered so that it is disposed around the groove of the implanted screw, the tapered post can then be removed from the screw, leaving an assembled bone plate and screw system.

Further features of the invention, its nature and various advantages, will be more apparent from the accompanying drawings and the following detailed description of the drawings and the preferred embodiments.

BRIEF DESCRIPTION OF THE DRAWINGS

The invention can be more fully understood from the following detailed description taken in conjunction with the accompanying drawings, in which:

FIG. 1A is an exploded view of a bone plate and screw system of the present invention;

FIG. 1B is a perspective view of the bone screw with the locking member and cap of FIG. 1A;

FIG. 1C is a cutaway view of an aperture of FIG. 1A having a screw, resilient locking member and cap nested therein;

FIG. 2A is an exploded view of the bone plate and screw system of FIG. 1A showing a plate first construction;

FIG. 2B is a detailed view of an aperture of FIG. 2A;

Figure 3:
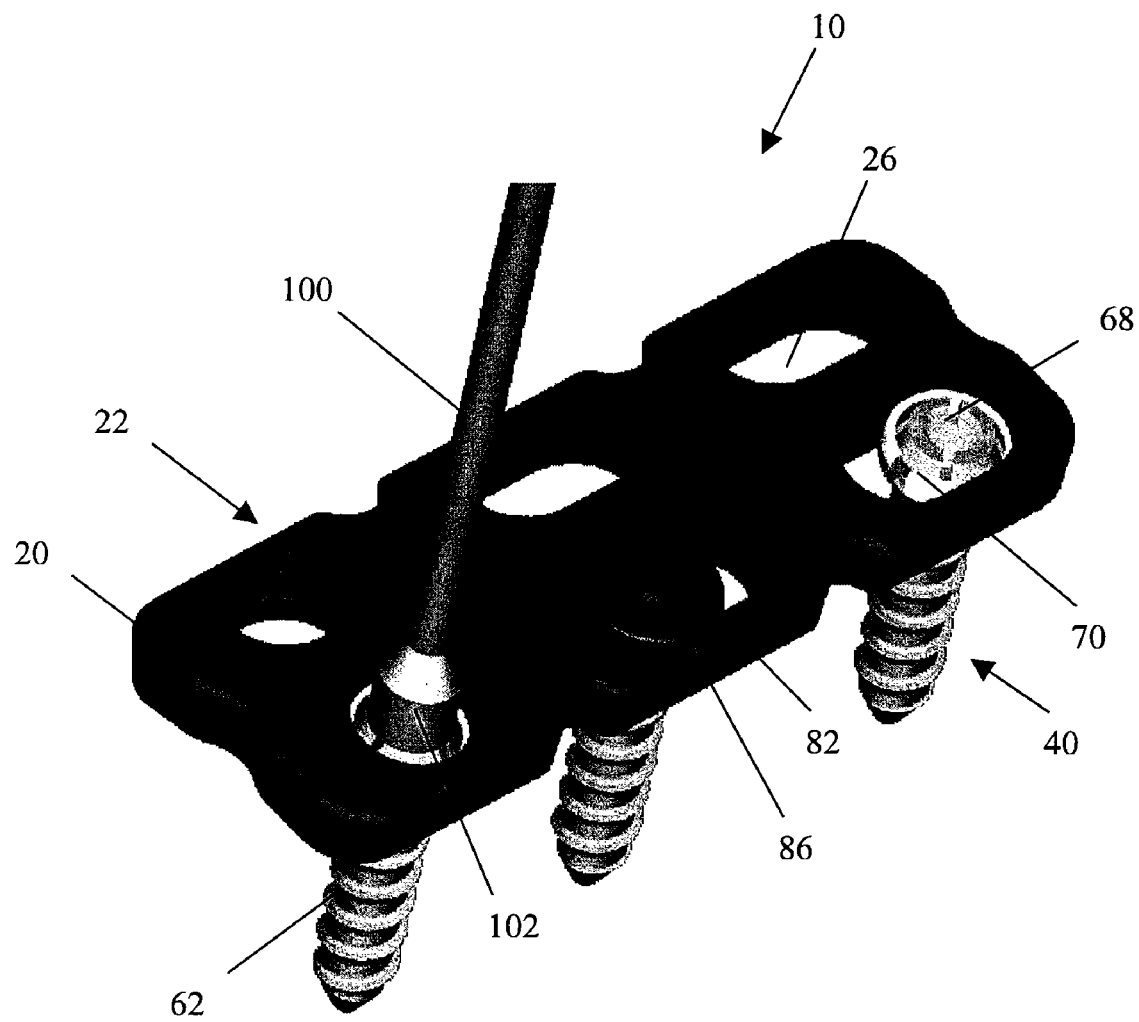
Figures 4A, 4B:
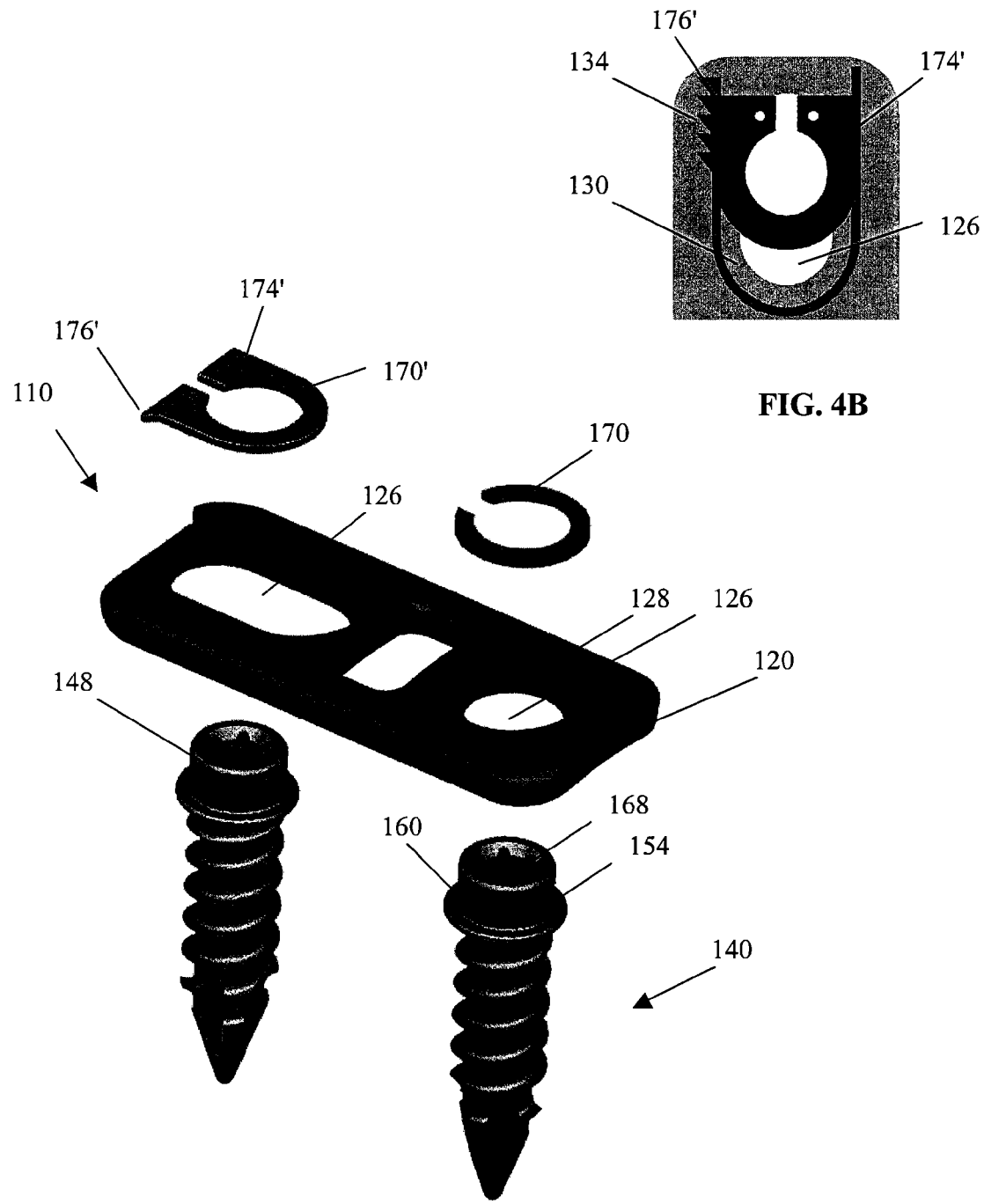
Figure 5A:
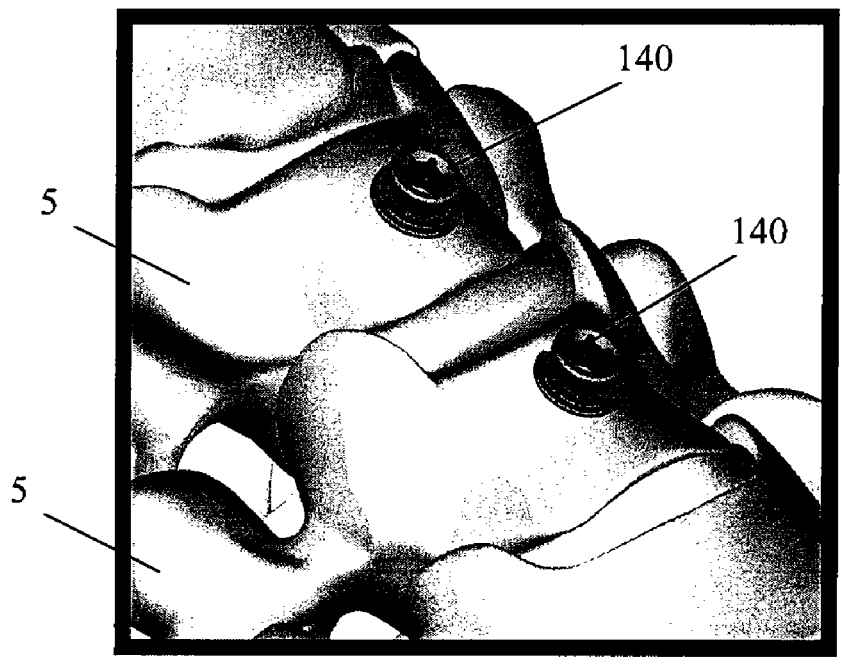
Figure 5B:
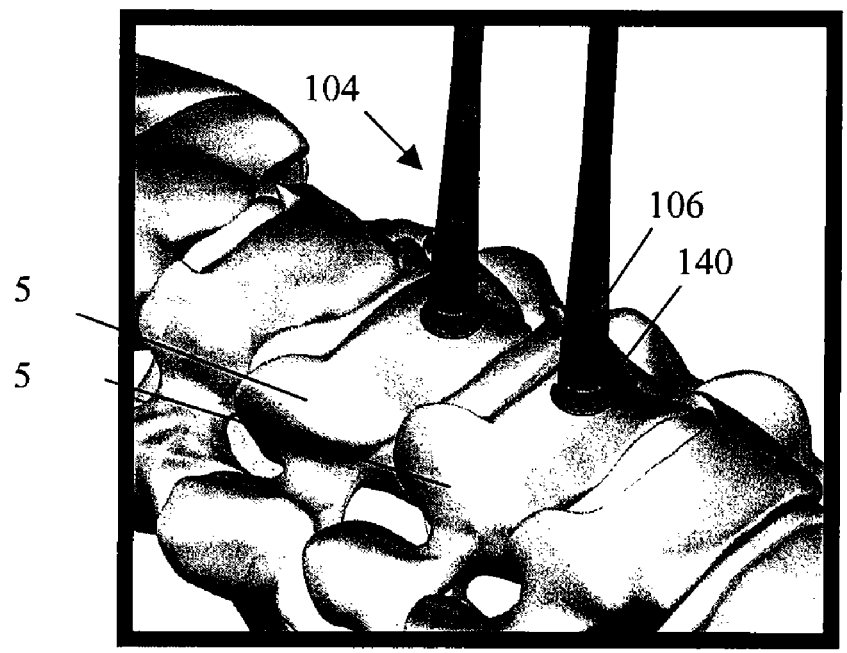
Figure 6A:
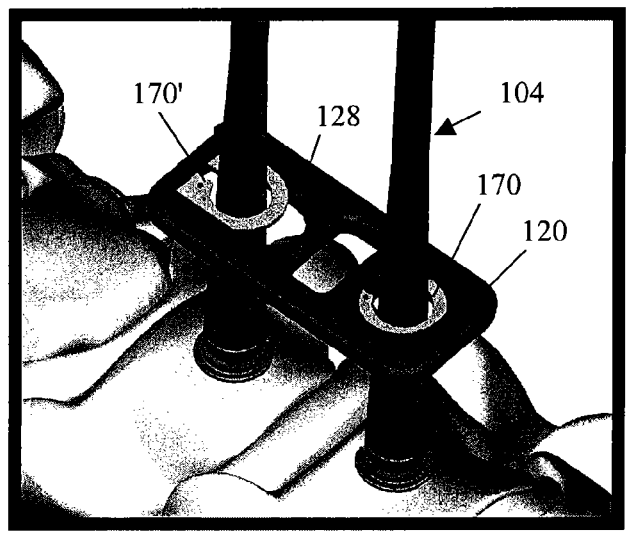
Figure 6B:
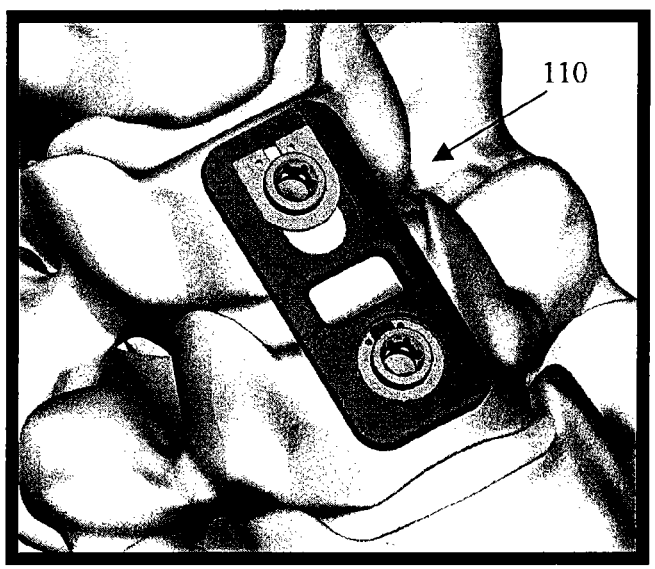
Figure 6C:
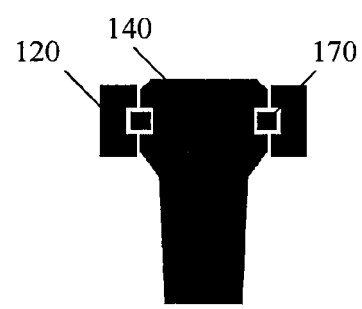
Figure 7A:
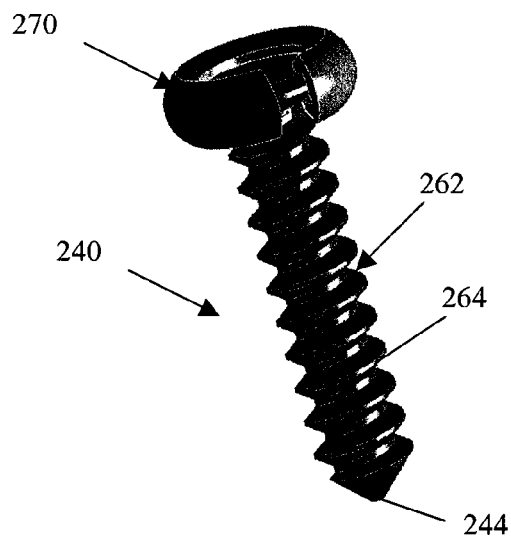
Figure 7B:
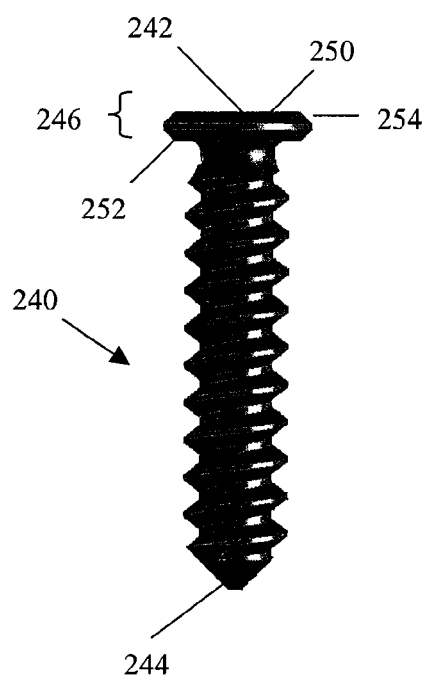
Figure 7C:
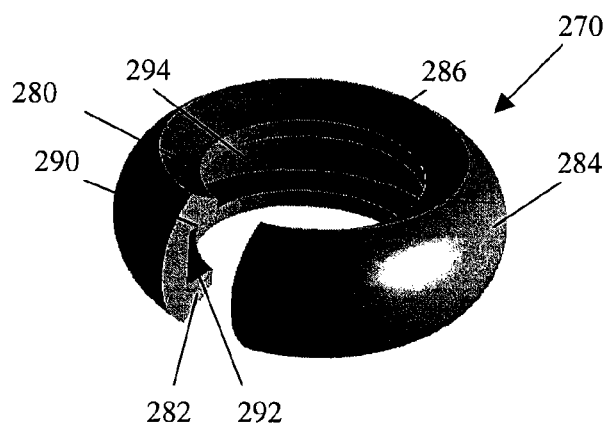
Figure 8A:
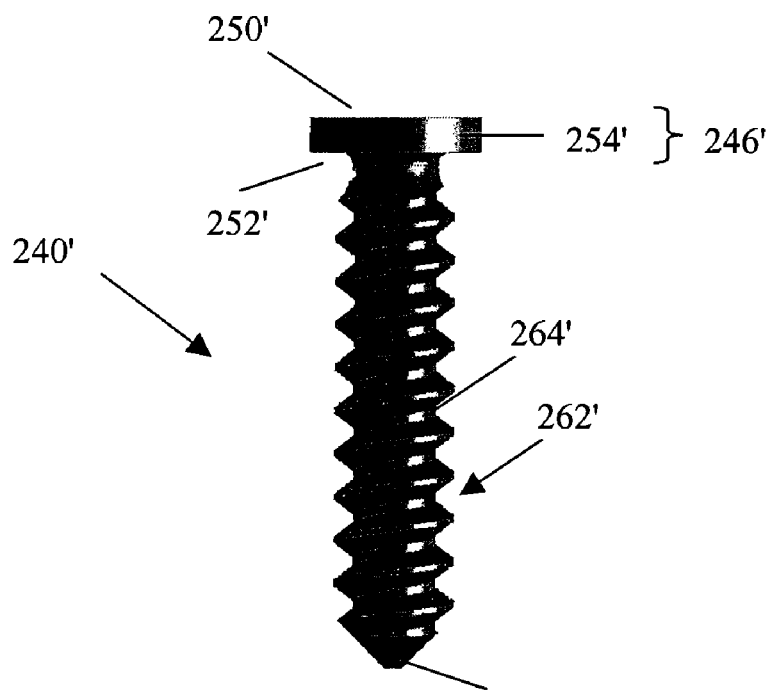
Figure 8B:
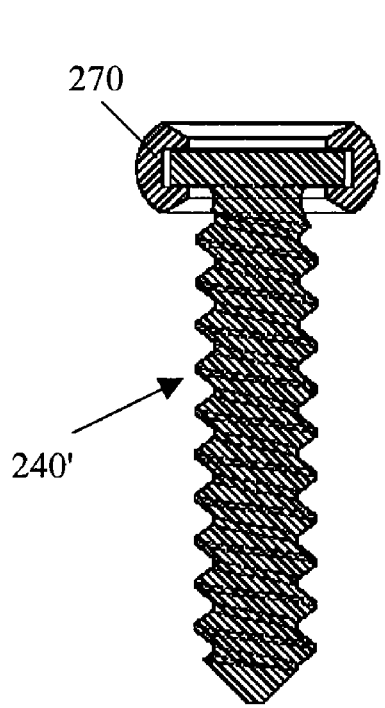
Figure 8C:
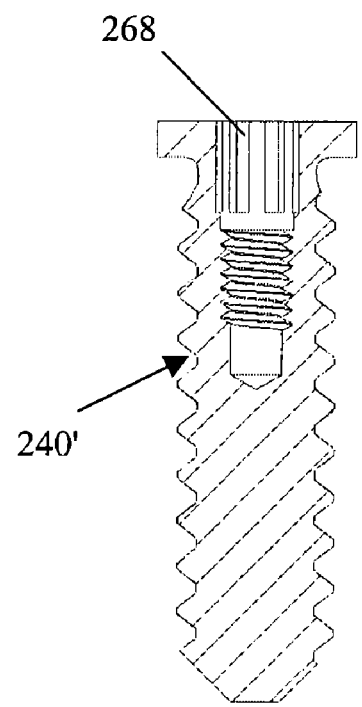
Figure 9A:
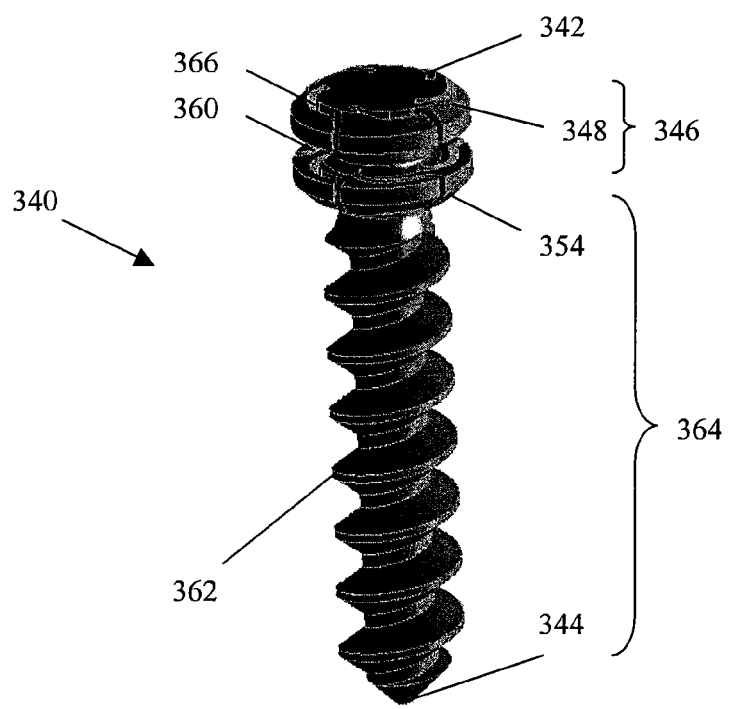
Figure 9B:
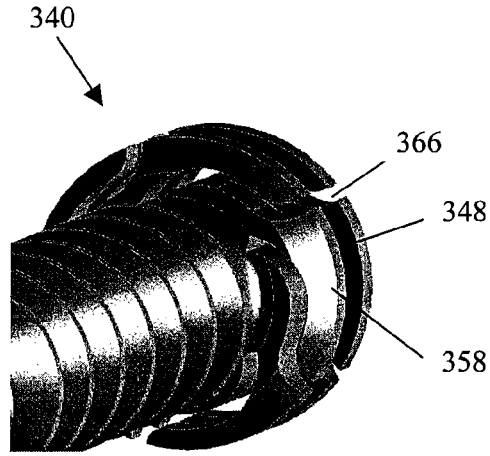
Figure 9C:
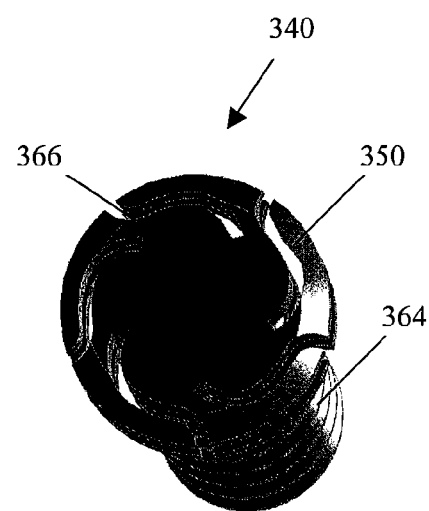
Figure 10A:
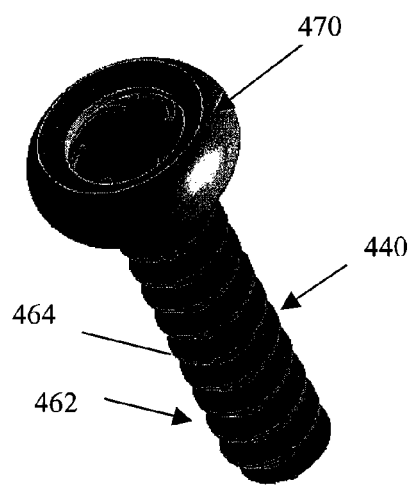
Figure 10B:
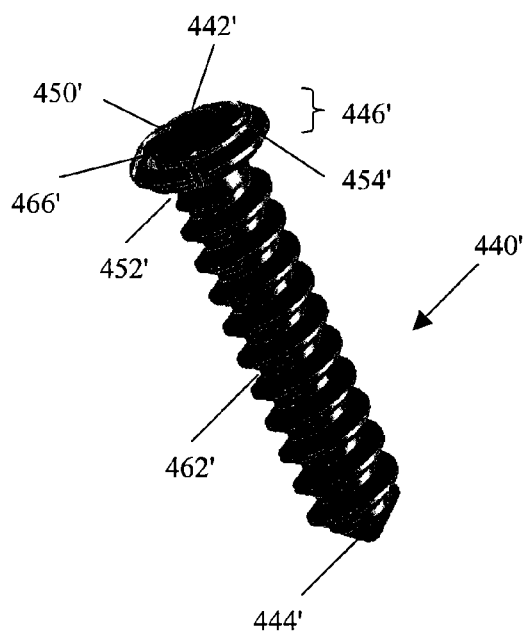
Figure 10C:
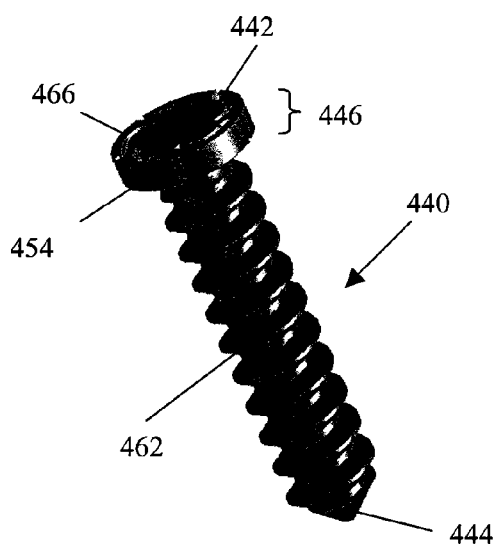
Figure 10D:
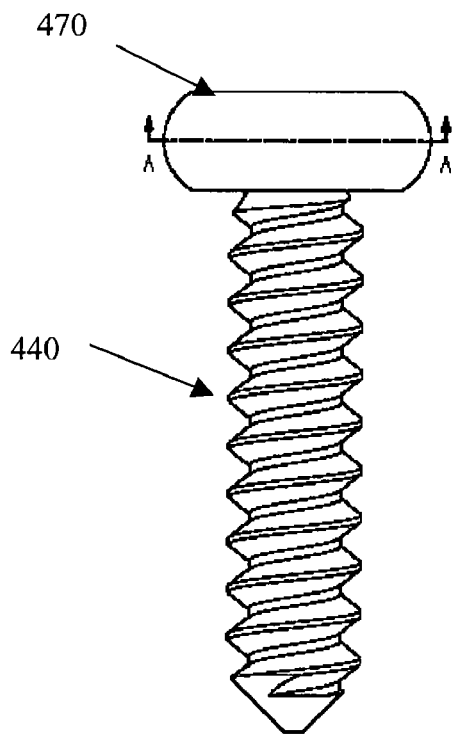
Figure 10E:
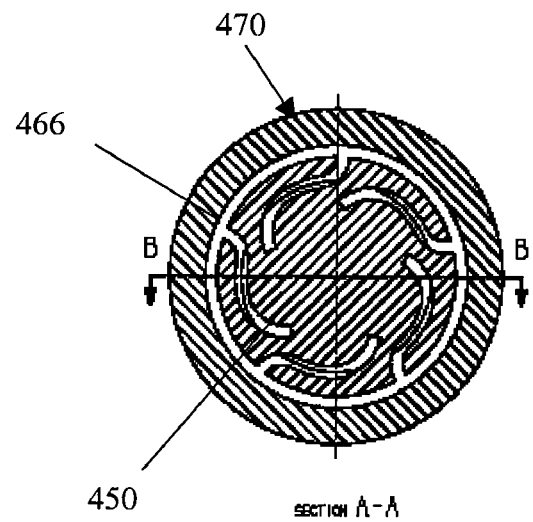
Figure 10F:
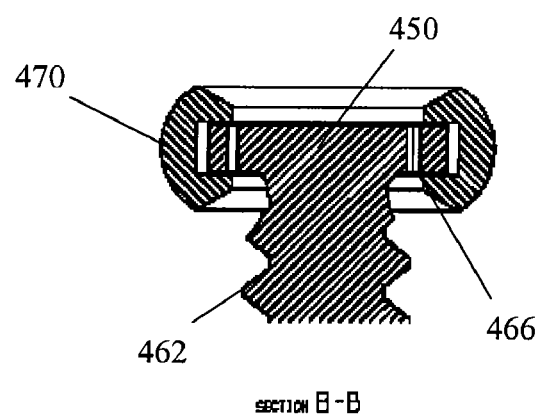
Figure 11A:
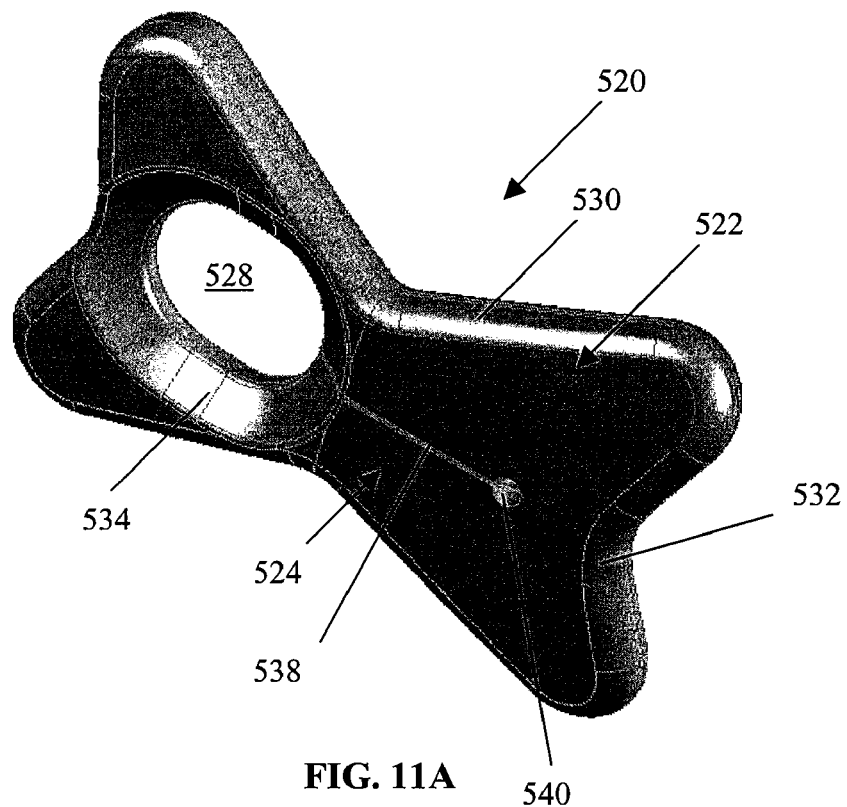
Figure 11B:
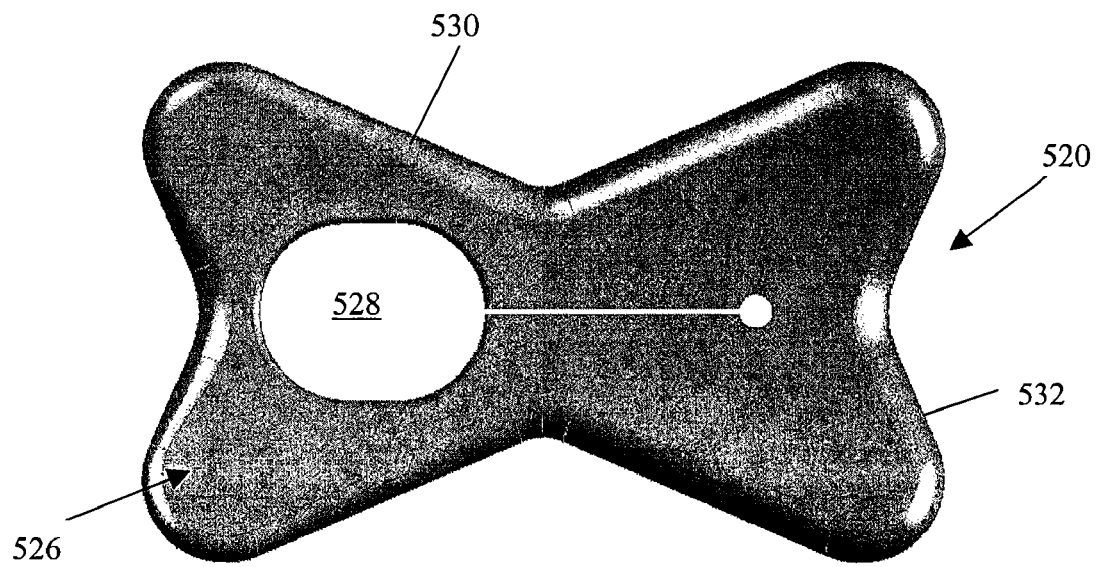
Figure 12A:
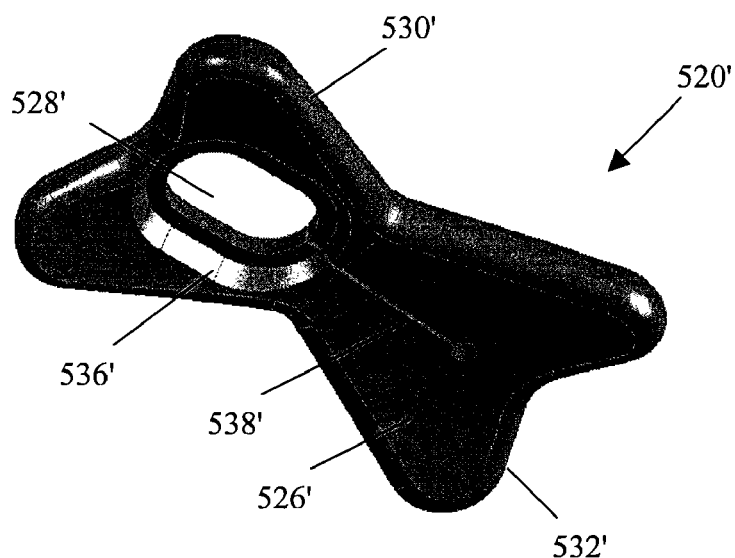
Figure 12B:
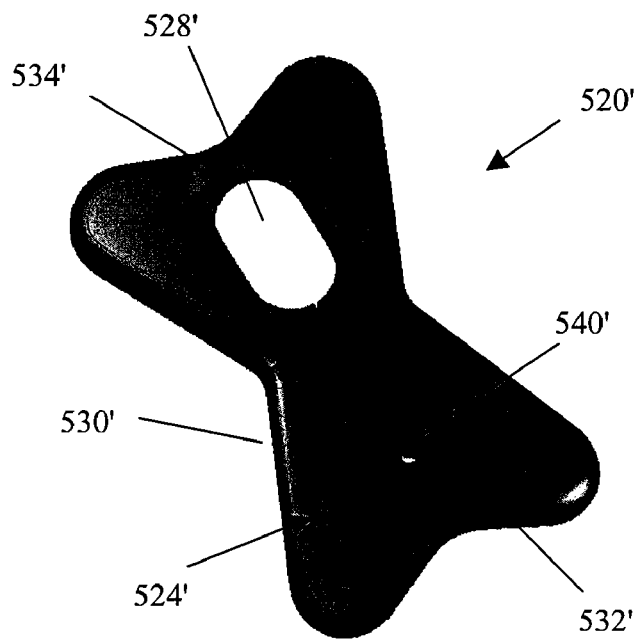
Figure 12E:
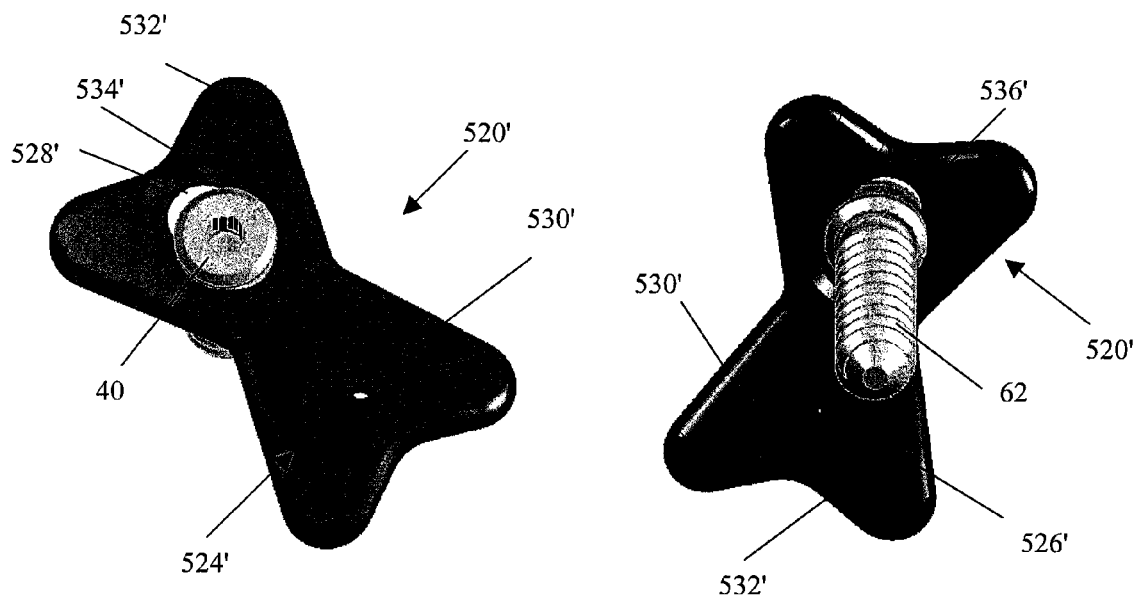
Figure 12E:
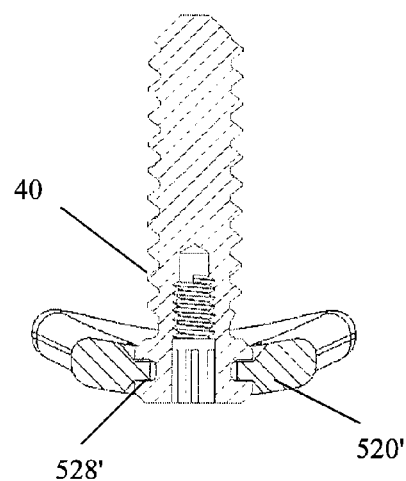
Figures 13A, 13B:
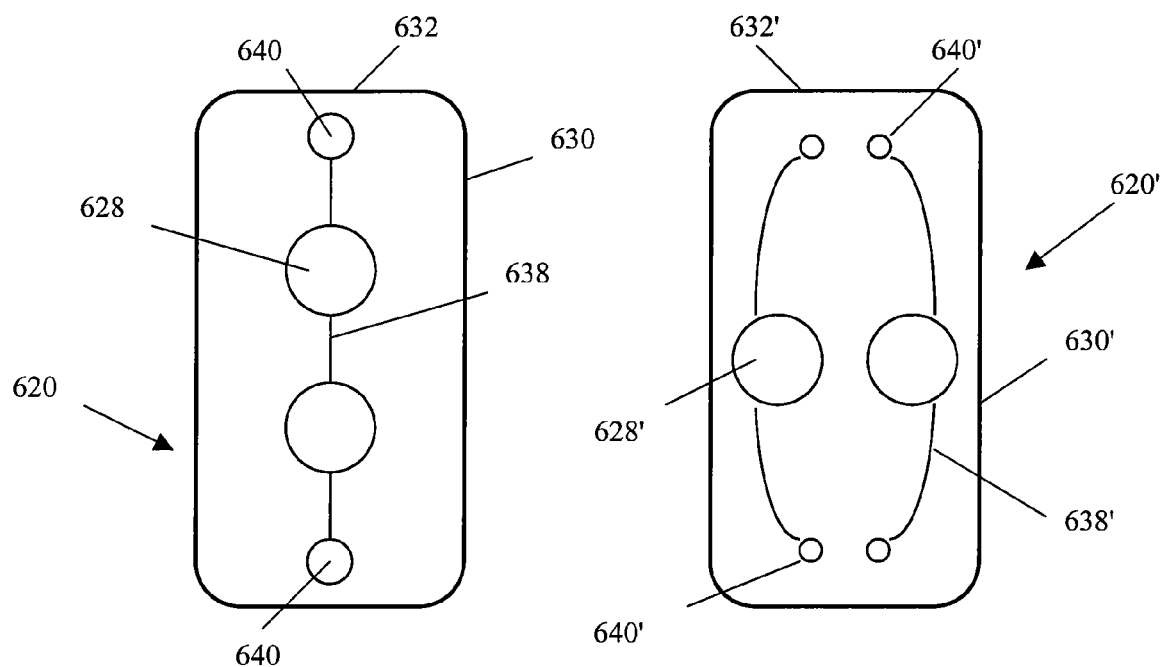
Figure 14A:
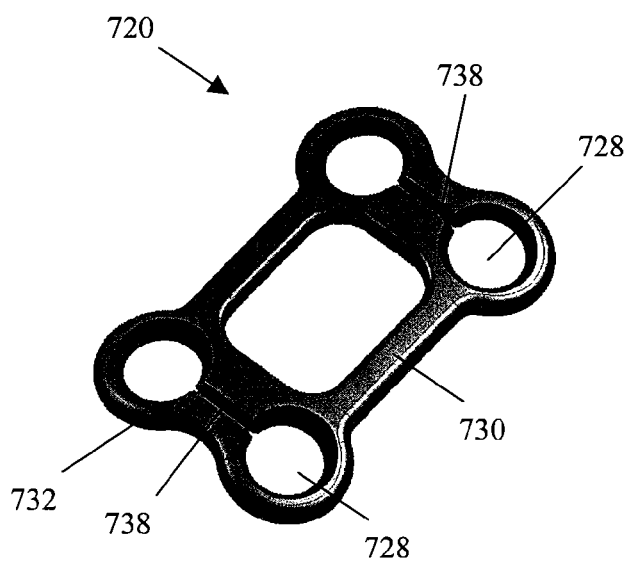
Figure 14B:
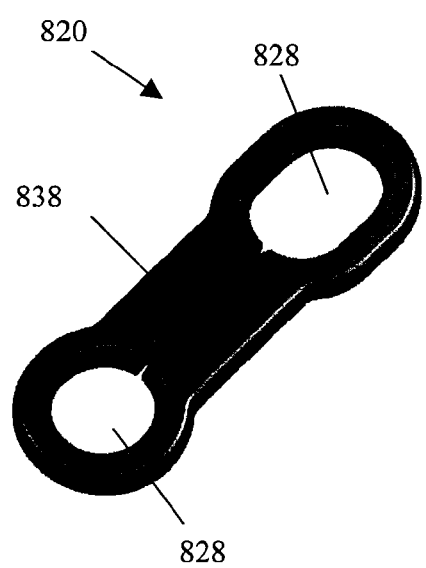

The invention can be more fully understood from the following detailed description taken in conjunction with the accompanying drawings, in which:

FIG. 1A is an exploded view of a bone plate and screw system of the present invention;

FIG. 1B is a perspective view of the bone screw with the locking member and cap of FIG. 1A;

FIG. 1C is a cutaway view of an aperture of FIG. 1A having a screw, resilient locking member and cap nested therein;

FIG. 2A is an exploded view of the bone plate and screw system of FIG. 1A showing a plate first construction;

FIG. 2B is a detailed view of an aperture of FIG. 2A;

FIG. 3 illustrates a method of assembling the bone screw and plate system of FIG. 1A;

FIG. 4A is a view of another embodiment of the bone plate and screw system of the present invention;

FIG. 4B is a detailed view of an aperture and locking member of FIG. 4A;

FIG. 5A illustrates a step in the method of applying the bone plate and screw system of FIG. 4A;

FIG. 5B illustrates another step in the method of applying the bone plate and screw system of FIG. 4A;

FIG. 6A illustrates yet another step in the method of applying the bone plate and screw system of FIG. 4A;

FIG. 6B illustrates a completely assembled and implanted bone plate and screw system of FIG. 4A;

FIG. 6C is a cross-sectional view of an aperture of FIG. 6B;

FIG. 7A is a perspective view of another embodiment of a bone screw and resilient locking member of the present invention;

FIG. 7B is a side view of the bone screw of FIG. 7A;

FIG. 7C is an enlarged view of the resilient locking member of FIG. 7A;

FIG. 8A is a side view of even another embodiment of a bone screw of the present invention;

FIG. 8B is a cross-sectional view of the bone screw of FIG. 8A along with the resilient locking member of FIG. 7C;

FIG. 8C is a cross-sectional view of the bone screw of FIG. 8A;

FIG. 9A is a perspective view of a bone screw for yet another embodiment of a bone plate and screw system of the present invention;

FIG. 9B is a bottom-up view of the bone screw of FIG. 9A;

FIG. 9C is a top-down view of the bone screw of FIG. 9A;

FIG. 10A is a perspective view of another embodiment of a bone screw and attachment member of the present invention;

FIG. 10B is a perspective view of another embodiment of the bone screw of FIG. 10A;

FIG. 10C is a perspective view of the bone screw of FIG. 10A;

FIG. 10D is a side view of the bone screw and locking member of FIG. 10A;

FIG. 10E is a cross-sectional view of the bone screw and locking member of FIG. 10D along lines A-A;

FIG. 10F is a cross-sectional view of the bone screw and locking member of FIG. 10E along lines B-B;

FIG. 11 is a perspective view of a bone plate for yet another embodiment of the bone plate and screw system of the present invention;

FIG. 11B is a bottom-up view of the bone plate of FIG. 11A;

FIG. 11C shows the bone plate of FIG. 11A with a bone screw;

FIG. 11D is a perspective view of the bone screw of FIG. 11C;

FIG. 11E is a cross-sectional view of the bone plate and screw of FIG. 11C along lines C-C;

FIG. 12A is a perspective view of another embodiment of a bone plate of the present invention;

FIG. 12B is a top-down view of the bone plate of FIG. 12A;

FIG. 12C is a top-down view of the bone plate of FIG. 12A with a screw;

FIG. 12D is a bottom-up view of the bone plate and screw of FIG. 12C;

FIG. 12E is a cross-sectional view of the bone plate and screw of FIG. 12C;

FIG. 13A is a schematic view of another embodiment of a bone plate of the present invention;

FIG. 13B is a schematic view of even still another embodiment of a bone plate of the present invention;

FIG. 14A is a perspective view of yet another embodiment of a bone plate of the present invention; and FIG. 14B is still another perspective view of an embodiment of a bone plate of the present invention.

DETAILED DESCRIPTION OF THE INVENTION

The present invention provides bone screws and bone plates that offer the surgeon the ability to either assemble the screws to the plate (i.e., plate first approach), or the plate to the screws (i.e., anchors first approach), depending on the surgeon's preference and the patient's anatomical situation. The bone screws and bone plates of the present invention include a combination of geometric configurations that allow the screws and plates to fit together from different assembly directions. Additionally, the bone screws and bone plates can include material resilience features to allow expansion/contraction during assembly for enabling bi-directional attachment to one another.

Turning now to the drawings and particularly to FIG. 1A, an exemplary bone plate and screw system 10 for stabilizing bone segments of the present invention is shown. In the illustrated embodiment, the system 10 includes a bone plate 20 defined by a first surface 22 and a second, bone-contacting surface 24 that is opposed to the first surface 22. The bone plate 20 can optionally be convexly curved along its length, enabling the bone plate 20 to conform to the curvature of natural vertebral bones. A plurality of apertures 26 extend through the first and second surfaces 22, 24 of the bone plate 20. Each of the apertures 26 has a predefined shape and size. For instance, each of the apertures 26 can be shaped like a hole or an elongated, or oblong, slot as illustrated. In addition, the rim 30 of the apertures 26 can be countersunk on the first surface 22 of the bone plate 20.

As shown in FIG. 1A, each of the apertures 26 is configured to receive one of a plurality of screws 40 configured to be inserted into bone. The screws 40 can be used to anchor the bone plate 20 to the particular bone segments that require fixation. Each of the screws 40 has a head region 46 at a proximal end 42. The head region 46 is defined by a top flange 48, a bottom flange 54, and a groove 60 located between the top and bottom flanges 48, 54 and extending about the circumference of the head region 46. The top flange 48 is defined by an upper surface 50 and a lower surface 52, while the bottom flange 54 is defined by an upper surface 56 and a lower surface 58. An elongated body 62 which includes a threaded portion 64 extends from the head region 46 to a distal end 44 of the screw 40.

To secure the bone plate 20 to the bone screws 40, a plurality of expandable and compressible locking members 70 are provided with the present bone plate and screw system 10. Each of the locking members 70 is resilient and, as illustrated in FIG. 1B, sized and shaped to mate with the groove 60 of the bone screws 40. As further shown in FIGS. 1A and 1C, each of the locking members 70 is configured to be disposed in a seating groove 28 within the aperture 26. The seating groove 28 lies between the first and second surfaces 22, 24 and runs about the circumference of the aperture 26 of the bone plate 20 to enable locking engagement of the bone plate 20 to the bone screws 40. While not illustrated as such, it is contemplated that the locking members can have a top surface that extends along a downward slope from an outer edge to an inner edge of the top surface, and a bottom surface that extends along an upward slope from an outer edge to an inner edge of the bottom surface. These chamfered features help to facilitate assembly of the bone plate and screw system.

As depicted in FIGS. 1A-1C, it is contemplated that each of the locking members 70 can comprise a C-ring or expandable snap ring for placement around the groove 60 of the bone screws 40 and for capture within the seating groove 28 of the apertures 26. The locking members 70 are capable of expanding and contracting to snap into the groove 60 of the bone screws. Each of the locking members 70 can also include a cutout portion 72 extending around the inner circumference for seating the top flange 48 of the bone screw 40. As shown in detail in FIG. 1C, the cutout portion 72 enables the top flange 48 of the head portion 46 to sit securely within the locking member 70, with the lower surface 52 of the top flange 48 resting against the cutout portion 72. Depending on its thickness, the locking member 70 can optionally include a cutout portion on its underside (not shown) mirroring the cutout portion 72 on the upper side to accommodate the bottom flange 54 of the bone screw 40. When surrounding the groove of the screw 40 and nested within the seating groove 28, the locking member 70 allows for translation in either direction and settling of the screw in to maintain compression across the bone/graft interface.

As shown in FIG. 1C, which depicts a cutaway view of the aperture of FIG. 1A directly above, top flange 48 can include a chamfered upper surface 50 and bottom flange 54 can include a chamfered lower surface 58. The chamfered surfaces 50, 58 of the bone screw 40 help facilitate the placement of the locking member 70 over the head region 46 and into the groove 60. The top flange 48 can also include a tool-engaging recess 66 extending vertically therethrough for engaging an insertion tool (not shown). In addition, each screw 40 can optionally have an open head region including a threaded bore 68 extending from an upper surface of the head region 46. The threaded bore 68 can be configured as either a hexagonal bore or a threaded bore, for example, to engage an inserter tool such as a post.

As an additional feature of the bone plate and screw system 10 of the present invention, a plurality of threaded caps 80 are provided, each of which are rigid and configured to engage with the threaded bore 68 of the head region 46. The threaded cap 80 can include a cap head 82 with an elongate, threaded body 84 extending therefrom. The threaded body 84 is configured to complement and mate with the threaded bore 68 of the bone screw 40. When threaded onto the head region 46 as illustrated in FIG. 1B, the threaded cap 80 provides further securement of the bone plate 20 to the bone screw 40.

The threaded cap 80 can have a tool-engaging bore 86 extending from an upper surface of the cap head 82 for engaging an inserter tool (not shown). As illustrated in FIG. 1C, the tool-engaging bore 86 can comprise a hexagonal bore. It is understood, however, that tool-engaging bore 86 can be configured with any suitable geometry, for example, as a threaded or hexagonal bore. The cap head 82 has a thickness that matches the depth of the countersunk or depressed rim 30 surrounding the apertures 26 on the first surface 22 of the bone plate 20. A nested region 32 along the countersunk or depressed rim 30 of the oblong apertures 26 helps capture and stabilize the threaded cap 80 within the aperture 26. The nested region 30 has surface features that include notches 34 at discrete locations along the rim 28. The notches 34 conform to the outer surface of the threaded cap 80, which together with the cap 80 allows the screw 40 within the oblong aperture 26 to be fixed at a discrete position. This feature is especially useful in spinal correction procedures where the bone segments to be fixed are selectively compressed or distracted over time, by moving the head region 46 of the screw 40 and its associated cap 80 along the nested region 32. As applied in FIGS. 1A and 1C, the cap head 82 sits flush against first surface 22 of the bone plate 20 to provide a smooth overall profile, avoiding damage to soft tissue surrounding the implant site.

The present system 10 is designed to allow versatile use of the different components, i.e., bone plate, screws, locking ring, cap, etc. in a number of combinations and configurations. Depending on the combination of components assembled, the bone screws 40 can be rigidly (i.e., no toggling, translation or rotation), semi-rigidly (i.e., rotation and toggling but no translation), or dynamically (i.e., translation and optionally rotation) fixed with the system 10 of the present invention. Thus, the surgeon or clinician using the present invention can select and provide for desirable biomechanical properties intraoperatively. The ability to control these biomechanical properties with the present system 10 is most desirable where the surgeon has to account for the natural settling of bone post-surgery.

In the present embodiment shown, apertures 26 are configured to allow relative fixation of the screws 40. In the case of the oblong apertures 26, the screws 40 are able to slide within the oblong aperture 26 until locked into place using the threaded cap 80 which would be captured within the surface features of the countersunk rim 30, e.g., notches 34 of the nested region 32 around the oblong apertures 26. The threaded cap 80, when captured within the notches 34 of the nested region 32, would thus restrict translation and/or rotation of the screw 40 within the aperture 26. In contrast, without the threaded cap 80, the screw 40 held by the locking member 70 alone would still be able to translate and rotate, but not toggle.

FIG. 2A depicts the bone plate and screw system 10 as applied with a plate first approach. Preferably, the resilient locking members 70 are already captured within the seating groove 28 of the apertures 26 of the bone plate 20 prior to assembly. The plate 20 with the captured locking members 70 is placed on the bone surface to be fixed. Next, the bone screws 40 are inserted into the bone segments using a conventional bone screw applicator (such as inserter tool 100 as shown in FIG. 3) through the captured locking member 70. The bone screws 40 can be pre-engaged to the applicator prior to this step. Using the screw applicator/post to insert the threaded portion 64 of the bone screw 40 through the captured resilient locking member 70, the surgeon can apply force to slide the bottom flange 54 of the screw 40 past the expandable locking member 70 until the head region 46 is nested within the locking member 70 and aperture 26 as shown in FIG. 1C. The resilient locking member 70, being captured within seating groove 32 of the aperture 26, thus secures the plate 20 to the bone screw 40 as the bone screw 40 is screwed into the bone segment to be fixed. Finally, the threaded cap 80 can be threaded into the threaded bore 68 of the bone screw 40 to provide rigid fixation of the bone screw 40 to the bone plate 20. Where the aperture 26 comprises an elongated or oblong slot, the nested region 32 along the countersunk rim 30 of the aperture 26 helps stabilize and lock in the threaded cap 80. As detailed in FIG. 2B, the nested region should complement a portion of the curvature of the outer surface of cap head 82 such that the cap head 82 sits snugly within the depressed or countersunk rim 30 of the elongated aperture 26. The nested region 32 with its surface features, i.e., notches 34, helps to avoid any sliding or migration of the bone screw 40 within the elongate slot.

FIG. 3 also depicts an approach for applying the same bone plate and bone screw system 10 of the present invention. In this procedure, bone screws 40 are first applied to the bone segments to be fixed, using a conventional bone screw insertion tool such as insertion tool 100 which has a threaded tip for engaging the threaded bore 68 of the bone screws 40. Preferably, each of the screws 40 is already engaged to the insertion tool 100 prior to assembly. As shown in FIG. 3, the insertion tool 100 can also include an enlarged tapered head 102 so that the tool 100 can also serve as an expansion post. The tool 100 can be preassembled with the screw 40, and the entire tool-screw combination can be placed within a cannulated instrument to be applied all at once. Alternatively, the bone screws 40 can be inserted into the bone segments to be fixed, and posts attached to their threaded bores 68 afterwards. Once the posts are in place, the bone plate 20 can then be placed over the bone screws 40, using the posts for aligning the apertures 26 over the implanted bone screws 40. The locking members 70 can already be captured within the seating groove 28 of each of the apertures 26 of the plate 20 prior to assembly. After the bone plate 20 is positioned over the implanted bone screw or screws 40, the plate 20 and the captured locking members 70 are slid down and over the enlarged tapered head 102. The tapered head 102, which has a maximum outer diameter larger than the resting inner diameter of the resilient locking member 70, will facilitate the expansion of the C-ring and enable the resilient locking member 70 to expand and slide over the top flange 48, then contract and snap back to nest within the groove 60 of the bone screw 40. Once disposed around groove 60 and captured within the seating groove 28 of the apertures 26, the resilient locking member 70 secures the bone plate 20 to the implanted bone screws 40. At this point, the bone screws 40 can be completely threaded into the bone segments, if they have not already been done so. Finally, threaded cap 80 can be applied to the threaded bore 68 of the bone screws 40 to further secure the bone plate 20 to the now implanted bone screws 40.

The ability of the bone plate and bone screw system 10 to be assembled as either a plate first or anchors first approach provides the surgeon with the flexibility to assemble the screw to the plate or the plate to the screw, depending on the surgeon's preference and the particular circumstances of the patient. By providing the surgeon with different assembly techniques, the present invention allows the surgeon more ways to align the bone plate and bone screws during surgery. Further through use of the optional threaded cap, the surgeon is provided with means to adjust the spacing between screws across the graft interface, e.g., to provide and maintain compression across the graft interface to enhance the environment to achieve bony fusion.

FIG. 4A illustrates another exemplary bone plate and screw system 110 in accordance with the present invention, in which a bone plate 120 is provided for assembly with bone screws 140 having non-resilient flanges 148, 154. The bone plate 120 can be secured to the bone screws 140 using resilient locking members 170. The bone screws 140 of this embodiment share similar features to the bone screws 40 of system 10, while the bone plate 120 shares similar features to the bone plate 20 of system 10; thus, similar elements are designated by the same number preceded by the suffix "1." One salient difference between the bone screws 40 of system 10 and the bone screws 140 of system 110 is that the top flange 148 of bone screws 140 is not chamfered. The bottom flange 154 of the bone screw is chamfered to accommodate a plate-first technique. However, in the assembly process which is described in detail below, tapered posts can be attached to the bone screws 140 to provide the chamfered surface needed to facilitate the expansion of the resilient locking member 170 over the top flange 148 of the bone screws 140.

As shown, the resilient locking member 170 can include an expandable/compressible C-ring which is configured to sit within the groove 160 of the bone screw 140. The resilient locking member 170 is configured to also nest within seating groove 128 of the round aperture 126 of the bone plate 120. For the oblong aperture 126 of the bone plate 120, a second type of resilient locking member 170' is provided. Resilient locking member 170' can also be a split ring for snapping into the groove 160 of the bone screw 140. The resilient locking member 170' also has enlarged end portions 174', with at least one of the enlarged end portions 174' including a notched edge 176'. As depicted in FIG. 4B, this notched edge 176' is configured to mate and engage with a ratcheted edge 134 running along a portion of the seating groove 128 of the oblong aperture 126. The ratcheted edge 134 enables the resilient locking member 170' and the bone screw 140 attached therewith to be maintained within the elongated aperture 126 to ratchet in discrete increments with respect to the length of the aperture 126. Such features provide the surgeon with even more flexibility with respect to the manner of assembling the bone plate and screw system 110. These features also provide a clinical benefit to maintain compression at the bone/graft interface.

As in the previous embodiment, the bone plate and screw system 110 of the present invention can be assembled using either a plate first or an anchors first approach as described above. In an anchors first approach where the bone plate 120 is assembled to the implanted bone screws 140, the bone screws 140 are implanted into the bone segments to be fixed. As shown in FIG. 5A, it is preferable to use a single bone screw 140 per vertebral body 5 to assist with proper alignment of the plate to the screws. However, it is understood that any number of bone screws 140 can be applied as deemed necessary by the surgeon, and as required by the particular bone plate to be used. After the bone screws 140 are applied, tapered posts 104 can be attached to the bone screws 140 as shown in FIG. 5B. Alternatively, the tapered posts 104 can be pre-engaged to the screws 140 prior to insertion. The tapered post 104 can extending into a thickened region 106 having a screw-engaging tip for engagement with a tool-engaging bore 168 extending from an upper surface of the top flange 148 of the bone screws 140. The tapered posts 104 can be used to align the bone plate 120, with the resilient locking members 170, 170' captured within the seated grooves 132 of the bone plate 120, onto the implanted bone screws 140, as illustrated in FIG. 6A. The thickened region 106 of the posts 104 helps facilitate the expansion of the resilient locking members 170, 170' so that as the resilient locking members 170, 170' slide down the post 104, the C-rings gradually expand to slide over the top flanges 148 of the bone screws 140 and snap into their grooves 160. The resilient locking members 170, 170', which are nested within seating grooves 128 of the bone plate, now surround the grooves 160 of the bone screws 140 as depicted in FIG. 6C. After the bone plate 120 is sufficiently secured to the implanted bone screws 140, the posts can be removed to leave a fully assembled bone plate and screw system 110 as shown in FIG. 6B.

In another exemplary embodiment of the present invention, a bone screw 240 and locking ring 270 is provided as shown in FIGS. 7A-7C, for use with a bone plate such as the plate 20 of the system 10 previously described. Bone screw 240 is sized and shaped to be received within the apertures of the bone plate 20 to anchor the plate 20 to the particular bone segments that require fixation. Screw 240 has a head region 246 at a proximal end 242. The head region 246 is defined by an upper surface 250, a lower surface 252, and a sidewall 254 extending therebetween and connecting the upper and lower surfaces 250, 252. An elongated body 262 which includes a threaded portion 264 extends from the head region 246 to a distal end of the screw 240. As illustrated in FIGS. 7A and 7B, the upper surface 250 and the lower surface 252 of the head region 246 can be chamfered.

The bone screw 240 cooperates with a resilient locking member 270 as shown in FIG. 7A for securing the bone plate 20 to the screw 240. The resilient locking member 270 is sized and configured to be captured within the seating groove 28 of the aperture 26 of the bone plate 20. As with locking member 70 of the previous system 10, resilient locking member 270 can be formed as a C-ring, or an expandable snap ring. As shown in FIG. 7C, resilient locking ring 270 includes a top surface 280, a bottom surface 282, and an outer wall 284 extending therebetween and connecting the top and bottom surfaces, 280, 282. Top surface 280 can be formed so as to extend along a downward slope from an outer edge to an inner edge of the top surface 280. Likewise, bottom surface 282 can be formed so as to extend along an upward slope from an outer edge to an inner edge of the bottom surface. The slopes of the top and bottom surfaces 280, 282 help to facilitate insertion of the locking member 270 into or onto the head region 246 of the bone screw 240.

A channel 286 extends about the inner circumference of the locking ring 270. The channel 286 is sized and shaped to capture the head region 246 of the screw 240, and is defined by a top side 290, a bottom side 292, and an inner wall 294 connecting the top and bottom sides together. In FIG. 7C, the top and bottom sides 290, 292 extend at right angles with respect to the inner wall 294. Such a channel 286 provides for some movement of the head region 246 within the channel 286 itself. However, it is understood that top and bottom sides 290, 292 can be formed at angles with respect to the inner wall 294, thereby forming a closer fit with the bone screw 240 where the head region 246 includes chamfered surfaces such as is shown in FIG. 7B. In another aspect of the present invention, bone screw 240' can include a head region 246' having a sidewall 254' which extends at a perpendicular angle with respect to the upper and lower surfaces 250', 252' as shown in FIG. 8B. As best seen in FIG. 8B, the head region 246' of the bone screw 240' would be complementary in shape and size to the channel 286 of the resilient locking member 270, enabling both screw 240' and locking member 270 to work and cooperate in congruence together. Additionally, since the interface between the two components is flat, i.e., direct, the overall stability and integrity of the system is enhanced. In both the bone screws 240, 240' just described, a tool-engaging bore 268 extending from the upper surface 250, 250' of the screws can be provided, as illustrated in FIG. 8C.

While the bone plate and screw systems described above utilize a resilient locking member 70, 170, 270 to secure the screws to the plate, the present invention also provides a bone plate and screw system in which the bone screw itself is resilient. As illustrated in detail in FIGS. 9A-9C, a bone screw 340 is provided having a head region 346 at a proximal end 342 and an elongated body 362 extending from the head region 346 to a distal end 344 of the screw 340. Elongated body 362 includes a threaded portion 364 configured for insertion into bone. The head region 346 has a top flange 348, a bottom flange 354, and a groove 360 located between the top and bottom flanges 348, 354 and extending about the circumference of the head region 346. Like bone screw 40, the top flange 348 of screw 340 can include a chamfered upper surface 350 and the bottom flange 354 can include a chamfered lower surface 358. As shown in detail in FIG. 9B, each of the flanges 348, 354 are provided with relief slits 366 extending therethrough, which allow the flanges 348, 354 to have compressible diameters. The slits 366 can comprise any suitable shape, including wavy S-shaped slits as shown. While the relief slits 366 of the top flange 348 are illustrated in FIG. 9C as being aligned with respect to the relief slits 366 of the bottom flange 354, it is contemplated that the relief slits 366 can be offset to provide a more robust system. Though not shown, it is also understood that the screw 340 can include a tool-engaging bore such as with screw 40.

As with the previously described bone screws, bone screw 340 can be used to secure a bone plate onto a bone segment to be fixed. The bone plate should be of the type having a first surface, a second, bone-contacting surface opposed to the first surface, and an aperture extending through the first and second surfaces. The aperture should be sufficiently sized and shaped to receive the screw 340 and nest within the groove 360 between the two flanges 348, 354. The resiliency of the flanges 348, 354 enables bone screw 340 to be secured to a bone plate without the need for a locking member in both a plate first or an anchors first approach. For instance, in an exemplary method of using bone screw 340, the screw 340 can be inserted into a bone segment to be fixed in an anchors first approach. To allow for an anchors fist approach, at least the top flange of the bone screw should be resilient. Next, the aperture of the bone plate can be placed over a post attached to the screw 340 to align the bone plate to the implanted screw 340. The optional post can be attached to the screw 340 prior to or after insertion into the bone segment to assist with alignment of the screw to the aperture of the plate. After the aperture is disposed over the post, the bone plate is slid down the post and onto the screw. The flexibility of the top flange 348 enables the aperture to move over the flange 348 and nest within the groove 360 of the screw 340. Once the aperture is secured around the screw 340, the post can be removed from the screw.

Alternatively, the present system can also utilize an optional attachment member and a bone plate having a seating groove such as bone plate 20 described above. The attachment member helps to facilitate the engagement and cooperation of the bone screw 340 and the bone plate. The attachment member should be configured to nest within the seating groove 28 of the bone plate 20 and seat around the groove 360 of the screw 340. Preferably, the attachment member would be captured within the seating groove 28 of the bone plate 20 prior to assembly so that the step of securing the aperture 26 around the screw 340 would include securing the captured attachment member around the groove 360 of the bone screw 340. While not illustrated, it is contemplated that the attachment member can include a notched edge such as with locking member 170'. The seating groove of the bone plate can also include a ratcheted edge along its side to allow the notched edge of the attachment member to mate and incrementally move within the aperture itself. If desired, a threaded cap 80 can be attached to the bone screw 340 to limit movement of the screw 340 within the aperture 26 in the same manner described above.

FIGS. 10A-10F illustrate yet another embodiment of a bone screw 440 and locking member 470 of the present invention. Bone screw 440 includes a head region 446 at a proximal end 442 and an elongated body 462 extending from the head region 446 to a distal end 444 of the screw 440. The elongated body 462 includes a threaded portion 464 configured for insertion into bone. The head region 446 includes an upper surface 450, a lower surface 452, and a sidewall 454 extending therebetween and connecting the upper and lower surfaces 450, 452. As illustrated in FIG. 10C, the sidewall 454 can extend at a perpendicular angle with respect to the upper and lower surfaces 450, 452. FIG. 10B shows a similar bone screw 440' where the upper and lower surfaces 450, 452 are chamfered. Both screws 440, 440' are provided with relief slits 466, 466' that extend through the head region 446 to provide it with a compressible diameter. The slits 466 can comprise any suitable shape, including wavy S-shaped slits as shown. While it is not shown, it is understood that these bone screws 440, 440' can be provided with a tool-engaging recess and/or tool-engaging bore for attaching an insertion tool thereto.

Bone screw 440 can be used to secure a bone plate onto a bone segment to be fixed. The bone plate should be of the type having a first surface, a second, bone-contacting surface opposed to the first surface, and an aperture extending through the first and second surfaces. The aperture should be sufficiently sized and shaped to receive the screw 440 and also include a seating groove to capture the head region 446 of the screw 440. Preferably, the aperture of the bone plate should be countersunk on at least one of the first and second surfaces to accommodate and facilitate the engagement of the screw with the bone plate. The resiliency of the head region 446 enables bone screw 440 to be secured to a bone plate without the need for a locking member in both a plate first or an anchors first approach. For instance, in an exemplary method of using bone screw 440, the screw 440 can be inserted into a bone segment to be fixed in an anchors first approach. Next, the aperture of the bone plate can be placed over a post attached to the screw 440 to align the bone plate to the implanted screw 440. The post can be attached to the screw 440 prior to or after insertion into the bone segment. After the aperture is disposed over the post, the bone plate is slid down the post and onto the screw 440. The compressibility of the head region 446 enables the aperture to move over the head region 446. Once the head region 446 is captured within the seating groove of the bone plate, the post can be removed from the screw.

However, as shown in FIGS. 10A and 10D-10F, the bone screw 440 can be used in combination with an optional attachment member 470. The attachment member 470 helps to facilitate the engagement and cooperation of the bone screw 440 and the bone plate. Preferably, the attachment member 470 is similar to the locking member 270 shown in FIG. 7C but is a closed ring rather than a C-ring. The attachment member 470 can be captured within the seating groove of the bone plate prior to assembly so that placement of the aperture over the post also aligns the captured attachment member with the implanted screw 440. Once the attachment member 470 is moved down and over the resilient head region 446, the head region 446 can nest within the groove of the attachment member 470, as shown in FIGS. 10E and 10F. By providing a flat, complementary interface between the attachment member 470 and the head region 446 as detailed in FIG. 11C, the congruency and integrity of the interference fit is maintained. If desired, a threaded cap can be attached to the screw to limit its movement within the aperture.

The present invention also provides a bone plate and screw system in which the plate itself is resilient. As illustrated in FIGS. 11A and 11B, bone plate 520 has a resilient aperture 528 for use with a non-resilient bone screw for stabilizing bone segments to be fixed. The bone plate 520 includes a body 522 defined by a first surface 524, a second, bone-contacting surface 526 opposed to the first surface 524, and a resilient aperture 528 extending through the first and second surfaces 524, 526 whose material resilience enables bi-directional assembly of a bone screw and the bone plate 520. The aperture 528 is sized and configured to receive a bone screw such as exemplary bone screw 502 as shown in FIGS. 11C-11E. As illustrated in detail in FIG. 11D, bone screw 502 includes a proximal end 504, a distal end 506, a head region 512 defined by a flange 514, a groove 516 extending about the circumference of the head region 512, and a body 508 extend from the groove 516. The body 508 includes a threaded portion 510 configured for insertion into bone. The aperture 528 can be countersunk from a first surface 524 of the bone plate. The countersunk portion 534 of the aperture 528 can extend toward the second, bone-contacting surface 526 of the bone plate 520. As shown in FIG. 11E, the groove 516 of bone screw 502 is configured to mate with the aperture 528 of the resilient bone plate 520, while the flange 514 is configured to seat against the countersunk region 534 of the aperture 528.

To facilitate the opening of the aperture 528, a relief slit 538 is provided. The relief slit 538 extends through the first and second surfaces 524, 526 of the plate 520, and extends from the aperture 528 to a through-hole, or relief hole 540. The relief slit 538 and relief hole 540 provide the aperture 528 with the ability to expand and contract. As shown in FIG. 11B, the slit 538 can extend longitudinally through the bone plate 520. Plate 520 can be concavely curved along its longitudinal axis to provide a better fit with the natural contours of human bones. The body 522 can be defined by a pair of longitudinal sidewalls 530 connected by a pair of opposed lateral endwalls 532. As illustrated, a midsection of each of the longitudinal sidewalls extends 530 towards a central region of the body 522. Similarly, a midsection of each of the lateral endwalls 532 extends towards a central region of the body 522. This provides the body 522 with a shape similar to a bowtie. The aperture 528 can be configured as either a slot (as shown) to allow translation of the screw, or as a hole to provide a rigid fixed position for the screw within the plate.

FIGS. 12A and 12B illustrate another variation of the resilient bone plate of the present invention, in which the aperture 528' of bone plate 520' can also include a countersunk portion 536' from the second surface 526' of the plate 520'. In all other respects, the bone plate 520' shown is similar to the bone plate 520 previously described, with common features designated by the same numeral followed by the symbol "'." The resilient bone plate 520' of the present invention can be applied using a bone screw similar to the one illustrated in FIGS. 1A-1C, and described above as bone screw 40. FIGS. 12C-12E illustrate the bone plate 520' assembled with an exemplary bone screw 40. As shown in detail in FIG. 12E, the aperture 528' is sized and shaped to directly engage the groove 60 of the bone screw 40 for locking engagement.

Consistent with all of the bone plate and screw systems of the present invention, the flexibility of the aperture 528' enables the bone plate 520' to be assembled to bone screw 40 in either a plate first or an anchors first approach. To apply the bone plate 520' in an anchors first approach, the bone screw 40 can be inserted into the bone segment to be fixed. Using a post attached to the bone screw 40 as an alignment guide, the aperture 528 can be placed onto the post and slid down. The post can be attached either prior to or after insertion of the screw 40 into the bone segment. Preferably, the post can be tapered. As the plate 20 is slid down the post, the taper of the post opens up the resilient aperture 528', allowing the aperture 528' to move over the top flange 48 and snap into the groove 60 of the bone screw 40 as shown in FIG. 12E. Once the plate 520' is secured around the screw 40, the post can be removed. It is contemplated that the countersunk portion 534' can also include a nesting region similar to the one for bone plate 20. If desired, a threaded cap can be attached to the screw 40 to restrict movement of the screw 40 within the aperture 528'.

While described and illustrated with bone screw 40 having two flanges, it is understood that the resilient bone plate 520 of the present invention can be provided with a seating groove around the aperture 528. Such a feature would enable the bone plate 520 to be used with a bone screw having a single flange, similar to the bone screw 240' illustrated in FIG. 8A. Optionally, a locking member such as locking member 270 can be used with bone screw 240' to secure the bone plate 520 to the implanted bone screw.

FIGS. 13A and 13B illustrate yet more configurations for the resilient bone plate of the present invention, in which the resilient bone plate comprises a plurality of apertures, relief slits, and relief holes. As shown, bone plate 620 can be defined by a pair of longitudinal sidewalls 630 connected by a pair of opposed lateral endwalls 632. The bone plate 620 can include a plurality of apertures 628 connected together by a relief slit 638 which terminates into a pair of relief holes 640 as shown in FIG. 13A. An alternative pattern is shown in FIG. 13B, in which bone plate 620' can include a pair of longitudinal sidewalls 630' connected by a pair of opposed lateral endwalls 632'. Bone plate 620' includes a pair of relief slits 638', each relief slit 638' extending into at least one relief hole 640' and an aperture 628'.

Yet more configurations are illustrated in FIGS. 14A and 14B, in which a resilient bone plate 720 and a resilient bone plate 820 are shown. Resilient bone plate 720 includes a pair of lateral sidewalls 730 connected by a pair of opposed lateral endwalls 732. Relief slits 738 extend along the lateral endwalls 732, each relief slit 738 terminating at each end into an aperture 728. In FIG. 14B, resilient bone plate 820 includes a single relief slit 538 extending into apertures 828 at each terminal end. The aperture can be configured as either a slot to allow translation of the screw, or as a hole to provide a rigid fixed position for the screw within the plate. As shown, resilient bone plate 820 includes apertures 828 having both shapes.

All of the bone plate and screw systems of the present invention can be assembled together using either a plate first or an anchors first approach, with the latter approach being desirable to provide the benefits accorded with an anchors first approach as previously mentioned. Preferably, the system can be assembled bi-directionally using both a plate first and an anchors first construction. It is understood that the components of the systems of the present invention can be formed from any biocompatible material, including biocompatible metals and polymers. It is also contemplated that the components can equally comprise bioabsorbable and/or biodegradable materials. Likewise, all components are considered to require dimensions suitable for use as medical implants.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A bone plate and resilient screw system for the stabilization of bone segments, comprising:
    a bone plate having a first surface, a second, bone-contacting surface opposed to the first surface, and an aperture extending through the first and second surfaces, the aperture having a predefined shape and size, and being configured to receive a bone screw; and
    a resilient screw configured to be inserted into bone, the screw having a head region at a proximal end, the head region being defined by a top flange, a bottom flange, and a groove extending therebetween, and an elongated body extending from the head region to a distal end of the screw, the elongated body including a threaded portion;
    wherein at least one of the top and bottom flanges includes at least one curved relief slit extending non-radially into the flange such that the relief slit separates the flange into an outer peripheral portion and an inner portion such that at least one of the top and bottom flanges of the screw is resilient.

2. The system of claim 1, wherein both the top and bottom flanges are resilient.

3. The system of claim 1, wherein the relief slit is S-shaped.

4. The system of claim 1, wherein a proximal surface of the top flange is chamfered.

5. The system of claim 1, wherein a distal surface of the bottom flange is chamfered.

6. The system of claim 1, wherein the aperture of the bone plate further includes a seating groove therein.

7. The system of claim 6, further including an attachment member for securing the bone plate to the screw, the attachment member being configured to be captured within the seating groove of the aperture, and further being sized and shaped to mate with the groove of the screw.

8. The system of claim 7, wherein the attachment member is a closed ring.

9. The system of claim 1, wherein the screw has an open head region, the region including a tool-engaging bore extending from an upper surface thereof.

10. The system of claim 9, wherein the tool-engaging bore is a threaded bore.

11. The system of claim 9, wherein the tool-engaging bore is a hexagonal bore.

12. The system of claim 9, further including a cap configured to engage the tool-engaging bore.

13. The system of claim 12, wherein the cap comprises a head region and a threaded body extending therefrom.

14. The system of claim 12, wherein the cap further includes a tool-engaging bore extending from an upper surface of the head region.

15. The system of claim 12, wherein the aperture includes a countersunk rim on the first surface of the bone plate.

16. The system of claim 15, wherein the countersunk rim includes a nested region for capturing the cap.

17. The system of claim 16, wherein the nested region includes surface features to restrict movement of the cap.

18. The system of claim 16, wherein the cap restricts translation and/or rotation of the screw with respect to the aperture.

19. The system of claim 1, wherein the predefined shape of the aperture is selected from the group consisting of a hole and an oblong slot.

* * * * *